United States Patent [19]

Diaz et al.

[11] Patent Number: 4,707,541
[45] Date of Patent: * Nov. 17, 1987

[54] SYNTHESIS OF HGRF (SOMATOCRININ) IN LIQUID PHASE AND INTERMEDIATE PEPTIDES

[75] Inventors: Joseph Diaz, Perols; Henri Demarne, Montpellier; Roméo Roncucci; Paul-Henry Schmelck, both of Paris, all of France

[73] Assignee: Sanofi, Paris, France

[*] Notice: The portion of the term of this patent subsequent to Apr. 8, 2003 has been disclaimed.

[21] Appl. No.: 752,799

[22] Filed: Jul. 8, 1985

[30] Foreign Application Priority Data

Jul. 10, 1984 [FR] France ................................ 84 10965

[51] Int. Cl.$^4$ ............................................... C07K 7/10
[52] U.S. Cl. ................................................... 530/324
[58] Field of Search .......................................... 530/324

[56] References Cited

U.S. PATENT DOCUMENTS 4,415,558 11/1983 Vale, Jr. et al. ..................... 530/324
4,489,163 12/1984 Rivier et al. ......................... 530/324
4,517,181 5/1985 Ling et al. ........................... 530/324
4,529,595 7/1985 Rivier et al. ......................... 530/324
4,549,986 10/1985 Evans et al. ........................ 530/324

FOREIGN PATENT DOCUMENTS 0105759 4/1984 European Pat. Off. .
0107890 5/1984 European Pat. Off. .
0117034 8/1984 European Pat. Off. .
0122818 10/1984 European Pat. Off. .

OTHER PUBLICATIONS

Chem. Pharm. Bull. 32, No. 2, 739-743, 510-519, 520-529, 1193-1199 (1984).
Chemical Abstract, vol. 101, 1984, p. 80 Ref. No. 104311x, Columbus, Ohio U.S.; N. Ling et al.: "Isolation, Primary Structure, and Synthesis Of Human Hypothalamic Somatocrinin: Growth Hormone-Releasing Factor"& Proc. Natl. Acad. Sci. U.S.A. 1984, 81 (14), 4302-4306.
Chemical Abstracts, vol. 101, 1984, p. 86 Ref. No. 144228g, Columbus, Ohio, U.S. R. Guillemin et al.: Recent Prog. Horm. Res. 1984, "Somatocrinin, The Growth Hormone-Releasing Factor".
Chemical & Pharmaceutical Bullentin, vol. 32, No. 2, Fevrier 1984, pp. 520-529; Nobutaka Fujii et al.: "Studies On Peptides, CXVII. Solution Synthesis Of The Tetratetracontapeptide Amide Corresponding To The Entire Amino Acid Swquence Of Growth Hormone Releasing Factor, Somatocrinin".

Primary Examiner—Delbert R. Phillips
Attorney, Agent, or Firm—Stevens, Davis, Miller & Mosher

[57] ABSTRACT

A process for the synthesis, in liquid phase and by fragments, of hGRF 1-44 and hGRF 1-40. This process consists in coupling, one after the other and in the order of the sequence of the GRF, (1) on the one hand, the following fragments:

| | | |
|---|---|---|
| H—Ala—Arg—Ala—Arg—Leu—NH$_2$ | called Fragment A | hGRF (40-44) or alaninamide (40) |
| H—Gln—Glu—Arg—Gly—OH | called Fragment B'$_1$ | hGRF (36-39) |
| H—Glu—Ser—Asn—OH | called Fragment B'$_2$ | hGRF (33-35) |
| H—Ser—Arg—Gln—Gln—Gly—OH | called Fragment C | hGRF (28-32) |
| H—Leu—Gln—Asp—Ile—Met—OH | called Fragment D' | hGRF (23-27) |
| H—Arg—Lys—Leu—OH | called Fragment E'$_1$ | hGRF (20-22) | to obtain the peptide K$_1$ [(hGRF (20-44)] on the corresponding peptide having the sequence (20-40) and (2) on the other hand, the following fragments:

| | | |
|---|---|---|
| H—Gln—Leu—Ser—Ala | called Fragment F$_1$ | hGRF (16-19) |
| H—Tyr—Arg—Lys—Val—Leu—Gly OH | called Fragment G$_1$ | hGRF (10-15) |
| H—Ile—Phe—Thr—Asn—Ser—OH | called Fragment H$_1$ | hGRF (5-9) | to obtain the peptide J [hGRF (5-19)] and thereafter to couple together the peptides J and K$_1$ in order to form the peptide having the sequence hGRF (5-44) or hGRF (5-40) and finally to couple the resulting peptide with the peptide H-Tyr-Ala-Asp-Ala-H, called fragment I hGRF (1-4).

4 Claims, No Drawings

SYNTHESIS OF HGRF (SOMATOCRININ) IN LIQUID PHASE AND INTERMEDIATE PEPTIDES

The present invention relates to a synthesis of hpGRF (Somatocrinin) in liquid phase and intermediate peptides.

hpGRF (human Pancreatic Growth Hormone releasing Factor) or Somatocrinin is a peptide constituted by the chain formation of 44 amino acids. Its sequence is as follows:

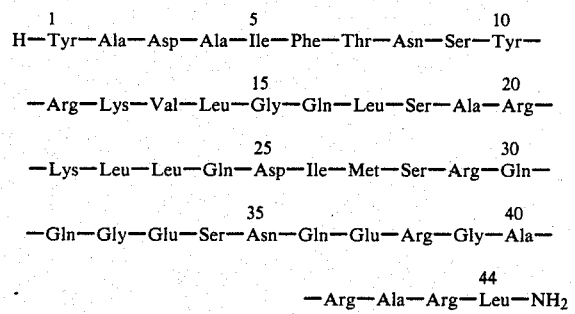

It has recently been discovered by A. GUILLEMIN et coll. (Science, 218, 585–587 (1982) from extracts of human pancreatic tumour.

This peptide is particularly active on the stimulation of the release of the growth hormone (GH) both in vitro and in vivo. In vitro, in particular, its effectiveness is shown at doses of some fento moles/ml ($ED_{50}=15$ fento moles/ml). The therapeutic interest of this substance in human medicine will therefore lie in the treatment of dwarfism and retarded growth in pediatrics. Other applications are possible in the cases of anabolic protein deficiency (stress-related ulcers, repair of fractures or of wounds of the cartilage, extensive burns (during the anabolic phase), cutaneous repairs, osteoporoses).

In the veterinary domain, the interest of this compound in the weight growth of farm-breeding animals (beef-cattle, sheep, pigs, chicken, . . . ) and in the increase in lactation (cows, ewes) is obvious.

The industrial development of this polypeptide compound necessitates the synthesis of large quantities of this substance. Conventional processes of synthesis in solid phase allow small quantities of this active principle to be prepared in short periods of time (Science, 218, 585–587 (1982) but at very high costs which are incompatible with a large-scale pharmaceutical development.

In its European Patent Application No. 122 818, the Applicant has already described a process of synthesis in liquid phase of Somatocrinin permitting the preparation of large quantities of this product.

It is the object of the present application to propose a novel process of synthesis permitting a considerable improvement of the rate of purity of the resulting intermediate peptides and, by way of consequence, facilitating the final purification phases and clearly improving the yields of pure Somatocrinin.

The process according to the present invention uses the following fragments:

| | | | |
|---|---|---|---|
| H—Ala—Arg—Ala—Arg—Leu—NH₂ | Fragment A | hGRF | (40–44) |
| H—Gln—Glu—Arg—Gly—OH | Fragment B'₁ | hGRF | (36–39) |
| H—Glu—Ser—Asn—OH | Fragment B'₂ | hGRF | (33–35) |
| H—Ser—Arg—Gln—Gln—Gly—OH | Fragment C | hGRF | (28–32) |
| H—Leu—Gln—Asp—Ile—Met—OH | Fragment D' | hGRF | (23–27) |
| H—Arg—Lys—Leu—OH | Fragment E'₁ | hGRF | (20–22) |
| H—Gln—Leu—Ser—Ala | Fragment F₁ | hGRF | (16–19) |
| H—Tyr—Arg—Lys—Val—Leu—Gly—OH | Fragment G₁ | hGRF | (10–15) |
| H—Ile—Phe—Thr—Asn—Ser—OH | Fragment H₁ | hGRF | (5–9) |
| H—Tyr—Ala—Asp—Ala—OH | Fragment I | hGRF | (1–4) |

Then, fragments A, B'₁, B'₂, C, D', E'₁ are coupled in the order of sequence of the hpGRF to obtain peptide K₁ hpGRF (20–44) and fragments F₁, G₁, H₁ likewise in the order of sequence of the GRF to obtain peptide J hpGRF(5–19).

Finally, the following are coupled in the right sequence:
5–19+20–44   5–44
1–4+5–44   1–44

The process according to the present invention is further characterized in that it includes the step of coupling, one after the other and in the order of sequence, the fragments in which:

(a) the side acid functions of the aspartic and glutamic acids and the side amine function of the lysine are protected by protector groups stable in the conditions of deprotection of the Boc group (tertiobutoxycarbonyl), (b) the guanidine function of the arginine is protected by protonation, and (c) the N-terminal amino acid is protected on the amine by the BOC group, (d) selectively eliminating the Boc group from the N-terminal amine of the peptide in elongation phase by hyrolysis with trifluoroacetic acid, said coupling being effected in an aprotic polar solvent, and at the end of sequence all the protector groups are eliminated by hydrolysis with the aid of a 0.1 to 1M solution of methanesulfonic or trifluoromethanesulfonic acid in trifluoroacetic acid.

The process of synthesis of the GRF is further characterized by the following features:

Application of the principle of minimum protection to the functionalized side chains.

With the exception of arginine in position 20, a temporary protection of the side guanidine function of the arginine by the nitro group is carried out. The aginine is introduced in sequence in the nitro guanidine form. The nitro function is the eliminated as soon as possible (see syntheisis of the fragments) by catalytic hydrogenation with the aid of Pd/charcoal, or else by using a generator of hydrogen such as formic acid or ammonium formate. In this way, except for position 20, all the synthesized fragments possessing arginine in their sequence have, at the end of synthesis, the quanidine functions simply protected by protonation with the aid of a strong acid (hydrochloric acid, for example).

The guanidine function of arginine in position 20 is protected by the MTS group (2,4,6-trimethyl phenylsulfonyl or mesityl-sulfonyl).

The carboxylic acid functions of the side chains of the glutamic as aspartic acid are protected by groups cleavable by catalytic hydrogenation ($H_2$/Pd/charcoal) or in a strong acid medium such as the methanesulfonic acid (0.5M)—trifluoroacetic acid, or trifluoromethanesulfonic acid (0.5 M)—trifluoroacetic acid mixtures. The applicants recommend as protectors benzyl (0 Bzl) or 2.6 dichlorobenzyl ester. These protector groups are stable in the conditions of intermittent deprotection of the amines in alpha (elimination of the t-butyloxycarbonyl (Boc)groups by trifluoroacetic acid).

The amine functions of the side chains of the lysines are protected by groups cleavable under the same conditions as previously. The applicants recommend the benzyloxycarbonyl (Z), 2-chloro or 2-bromo benzyloxycarbonyl (2 - Cl or 2 - Br Z) groups stable in the conditions of intermittent deprotection by trifluoroacetic acid.

The hydroxyl functions present in the threonine, serine and tyrosine are not protected.

The elongated of the peptide from the synthesized fragments is effected by using as coupling agent the hexafluorophosphate of benzotriazolyl oxyphosphonium (BOP), or dicyclohexyl carbodiimide in the presence of 1-hydroxy benzotriazole, or according to the method employing carboxyazides (Curtius), in an appropriate solvent such as dimethyl formamide or dimethylsulfoxide. Isolation of the product from the reaction medium is effected by introducing a third solvent which renders insoluble (ether, ethyl acetate, ... ) which precipitates the peptide.

One is limited during the steps of coupling to summary purifications of the solid-phase washing type with the aid of appropriate solvents in order to eliminate the slight excess of the last coupled fragment, as well as the impurities brought by the coupling agents.

Each fragment coupling operation is followed by a phase of intermittent deprotection of the Boc (tertiobutyloxy carbonyl) protector group, at the level of the amine on which the following coupling will be effected. Such deprotection is ensured by trifluoroacetic acid in methylene chloride (50/50 by volume).

The deprotections of the side chains at the end of elongation of the peptide may be effected by hydrogenation in the presence of a catalyst (such as Pd/C) with the aid of gaseous hydrogen under a slight pressure (1 to 5 kg) or with a generator of hydrogen such as formic acid or ammonium formate. It is also possible to eliminate this type of protector group by a strong acid such as the mixture of methanesulfonic acid in trifluoroacetic acid (0.5M) or of trifluoromethanesulfonic acid in trifluoroacetic acid (0.5M).

The product, after the terminal deprotections, is purified by filtration over Sephadex gel G 50 with the aid of 30% acetic acid. The GRF 1-44 enriched fractions are gathered together and subjected to a chromatography on ion exchangers (cations) of the carboxy type and with the aid of a gradient with increasing ionic force adapted to the type of ion exchanger resin used. The fractions of highest purity are gathered together and purified, either by partition chromatography on an appropriate support of the Sephadex G 50 or Biogel P 10 type, or by counter-current distribution.

The fractions of which the titer of purity is judged satisfactory by analytic HPLC are gathered together. The others are recycled.

A variant of the process consists in replacing the partition chromatography or counter-current distributon by preparative HPLC.

The process according to the present invention can also be applied to the synthesis of GRF 1-40, a natural product also isolated by R. GUILLEMIN, nearly as reactive as GRF 1-44 and usable in the same therapeutic indications in which case the fragment A hpGRF (40-44) is replaced in the aforesaid synthesis with analinamide (H-Ala-NH$_2$).

The invention also relates to the intermediate peptides or fragments of the following formulae:

Boc—Gln—Glu(O Bzl)—Arg—Gly—OH;
X—Gln—Glu—Arg—Gly—OH;
Boc—Glu—(O Bzl)—Ser—Asn—OH;
X—Glu—Ser—Asn—OH;
Boc—Leu—Gln—Asp(O Bzl)—Ile—Met—OH;
X—Leu—Gln—Asp—Ile—Met—OH;
Boc—Arg(MTS)—Lys(Z)—Leu—O CH$_3$;
X—Arg—(MTS)—Lys(Z)—Leu—NH—NH$_2$;
X—Gln—Glu(O Bzl)—Arg—Gly—Ala—Arg—
　　　　　　　　　　—Ala—Arg—Leu—NH$_2$;
X—Glu(O Bzl)—Ser—Asn—Gln—Glu(O Bzl)—Arg—Gly—Ala—
　　　　　　　　　—Arg—Ala—Arg—Leu—NH$_2$;
X—Ser—Arg—Gln—Gln—Gly—Glu(O Bzl)—Ser—Asn—Gln—
　　—Glu(O Bzl)—Arg—Gly—Ala—Arg—Ala—Arg—Leu—NH$_2$;
X—Leu—Gln—Asp(O Bzl)—Ile—Met—Ser—Arg—Gln—Gln—
　　—Gly—Glu(O Bzl))Ser—Asn—Gln—Glu(O Bzl)—Arg—Gly—
　　　　　　　　　　—Ala—Arg—Ala—Arg—Leu—NH$_2$;
X—Arg(MTS)—Lys(Z)—Leu—Leu—Gln—Asp(O Bzl)—Ile—
　　—Met—Ser—Arg—Gln—Gln—Gly—Glu(O Bzl)—
　　—Ser—Asn—Gln—Glu(O Bzl)—Arg—Gly—Ala—
　　　　　　　　　　—Arg—Ala—Arg—Leu—NH$_2$;
X—Ile—Phe—Thr—Asn—Ser—Tyr—Arg—Lys(Z)—
　　—Val—Leu—Gly—Gln—Leu—Ser—Ala—Arg(MTS)—
　　—Lys(Z)—Leu—Leu—Gln—Asp(O Bzl)—Ile—Met—Ser—Arg—
　　—Gln—Gln—Gly—Glu(O Bzl)—Ser—Asn—Gln—Glu(O Bzl)—
　　　　　—Arg—Gly—Ala—Arg—Ala—Arg—Leu—NH$_2$, in which X is H or Boc.

The invention further relates to the protected hpGRF 1-44 of formula:

Y—Tyr—Ala—Asp (O Bzl)—Ala—Ile—Phe—Thr—Asn—Ser—

Tyr—Arg—Lys (Z)—Val—Leu—Gly—Gln—Leu—Ser—Ala—

Arg (MTS)—Lys (Z)—Leu—Leu—Gln—Asp (O Bzl)—Ile—Met—

Ser—Arg—Gln—Gln—Gly—Glu (O Bzl)—Ser—Asn—Gln—

Glu (O Bzl)—Arg—Gly—Ala—Arg—Ala—Arg—Leu—NH$_2$, in which Y is H, Z or Boc, as well as to the likewise protected hpGRF 1-40.

The synthesis strategy which characterizes the present invention is summed up hereinafter in diagrams I, II and III.

Tables I to X give the synthesis diagrams of the basic fragments:

TABLE I (fragment A)

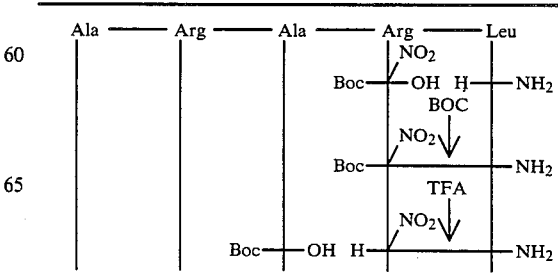

TABLE I-continued
(fragment A)
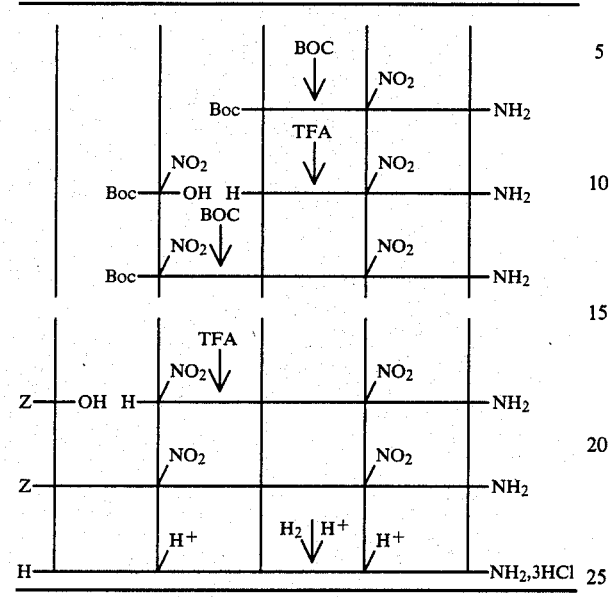
TABLE II
(Fragment B'₁)
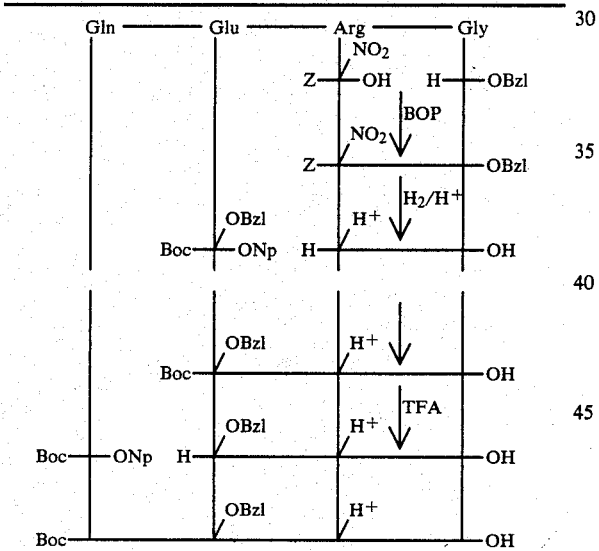
TABLE III
(fragment B'₂)
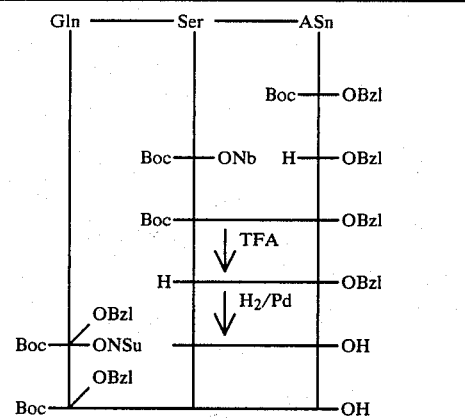
TABLE IV
(Fragment C)
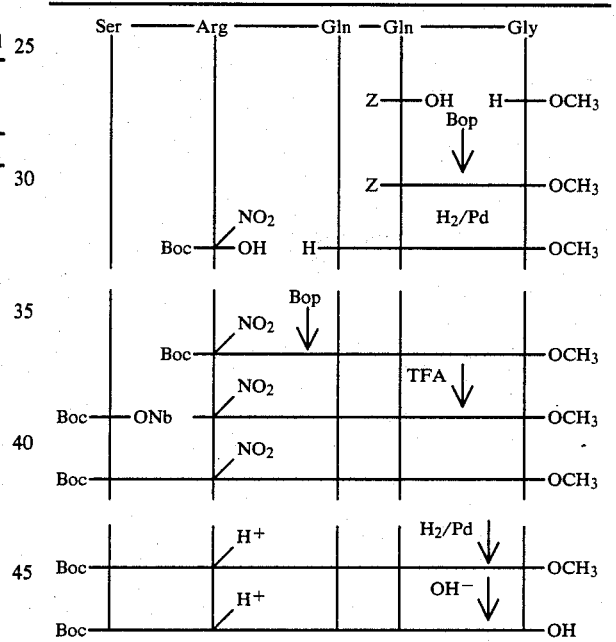
TABLE V
(fragment D')
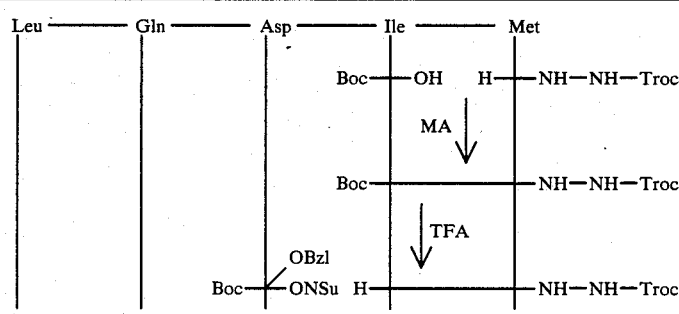

TABLE V-continued
(fragment D')
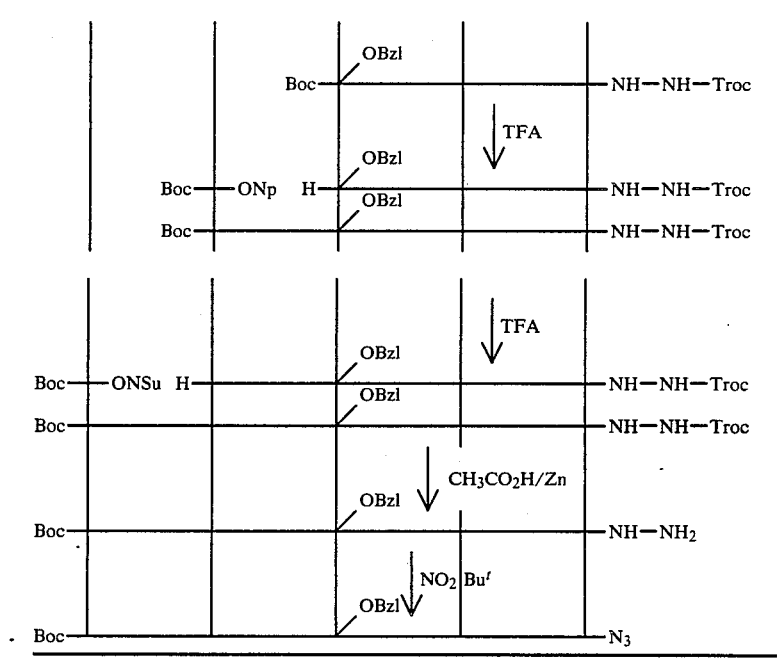
TABLE VI
(fragment E'₁)
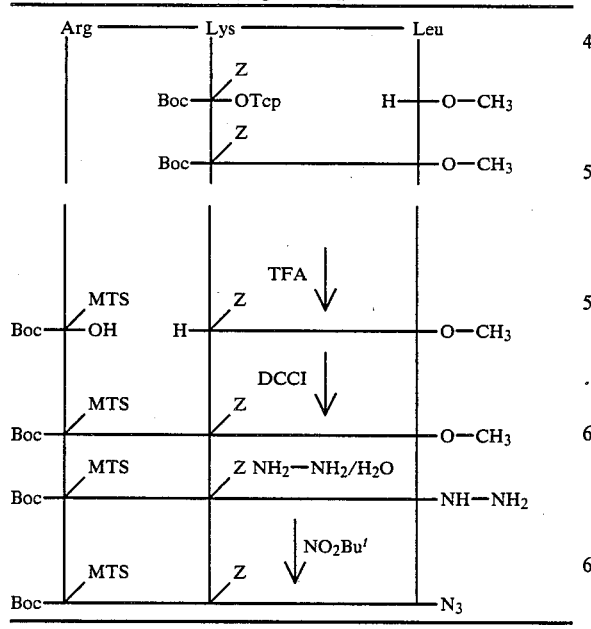
TABLE VII
(fragment F₁)
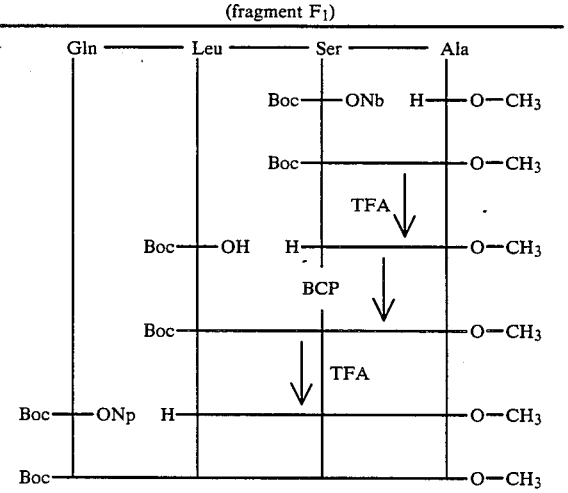

TABLE VIII
(fragment G₁)
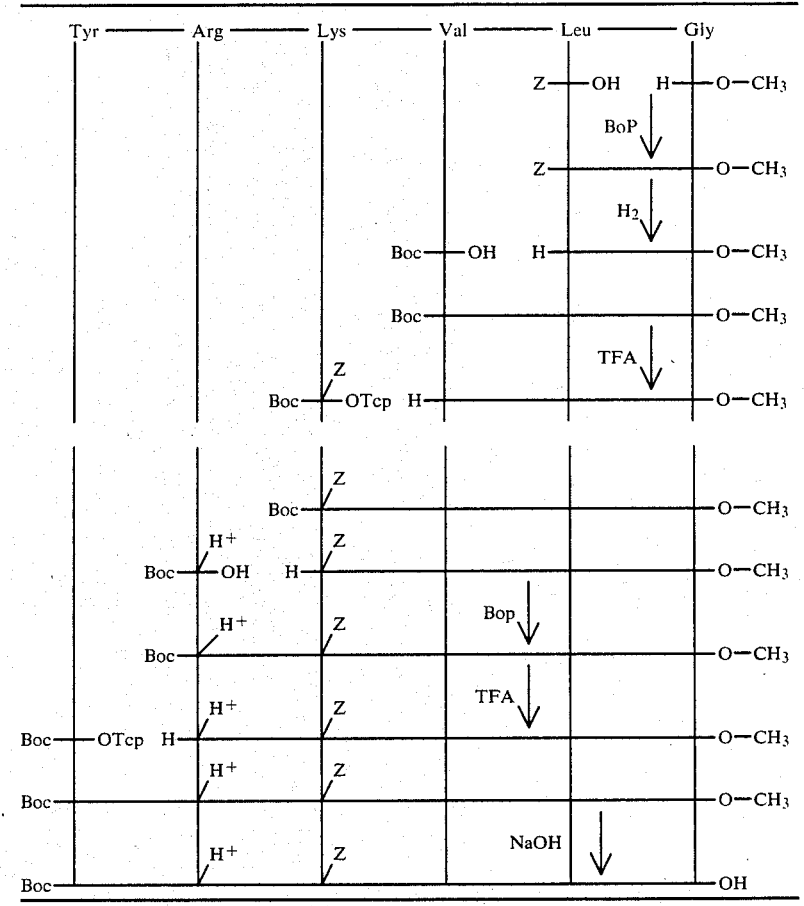
TABLE IX
(fragment H₁)
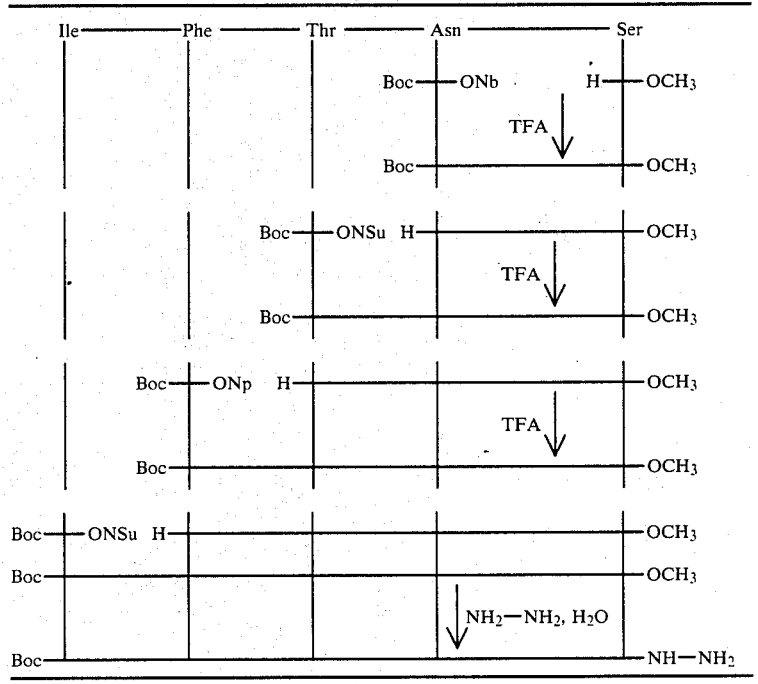

TABLE X
(fragment I)
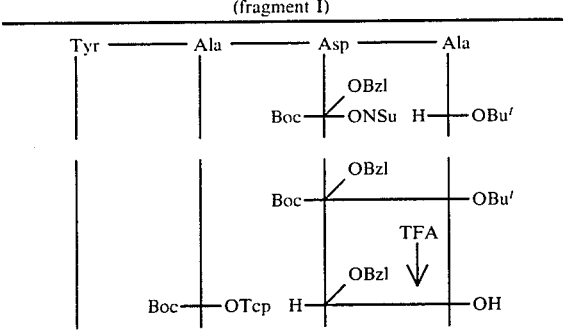
TABLE X-continued
(fragment I)
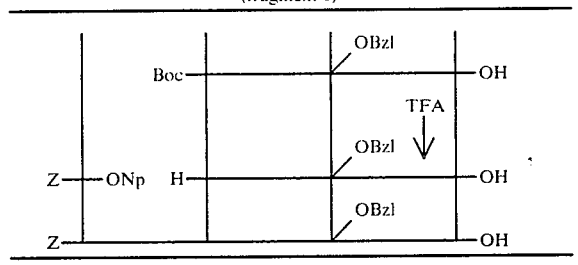
DIAGRAM I
SYNTHESIS OF PEPTIDE (K₁(hpGRF 20-44)
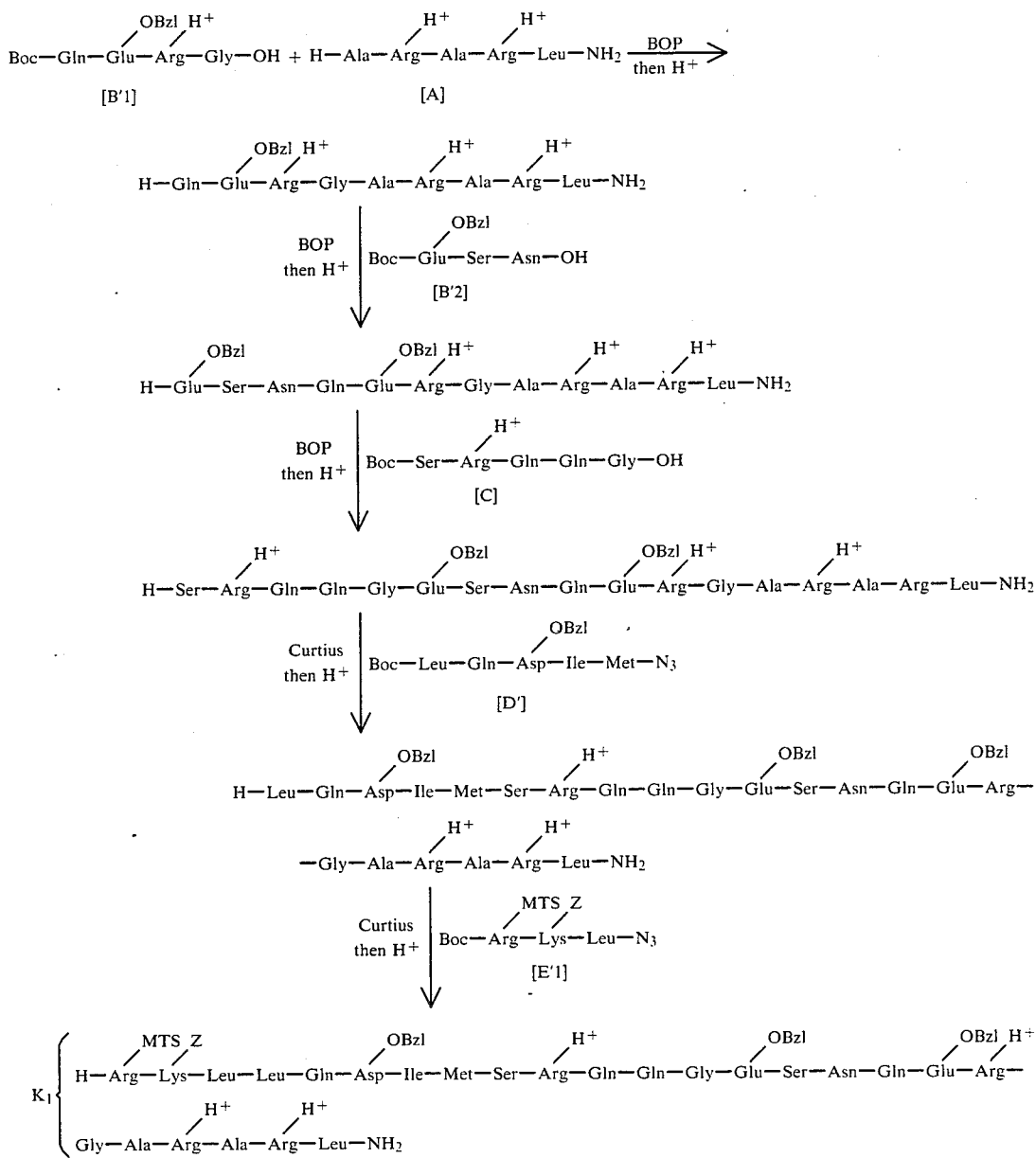
DIAGRAM II
SYNTHESIS OF PEPTIDE J hpGRF (5-19)

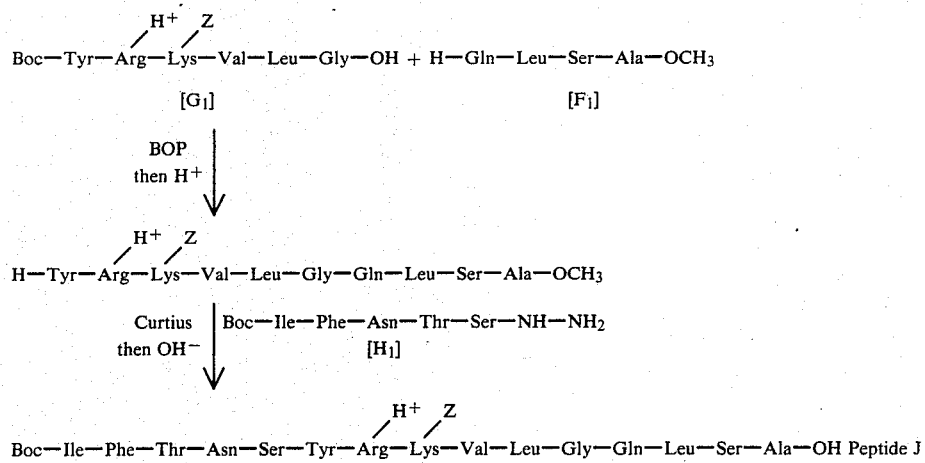

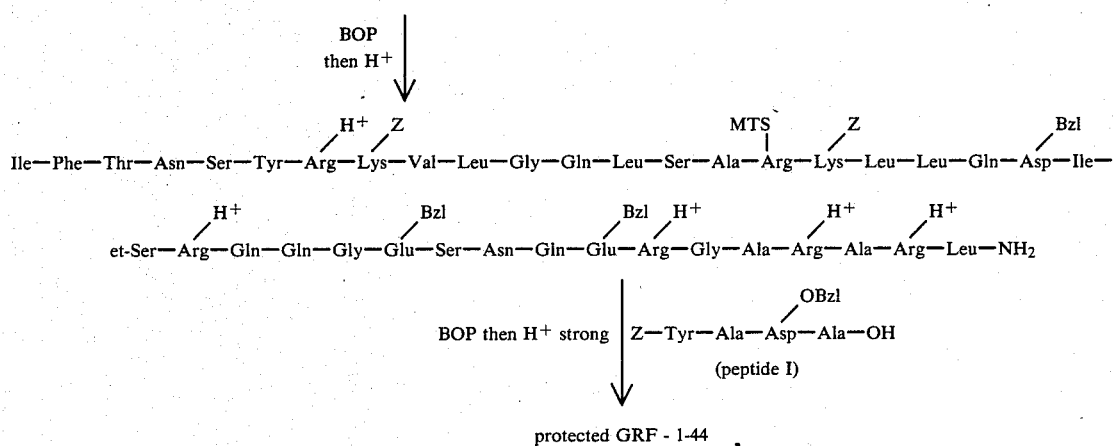

The following examples will enable the scope of the invention to be more readily understood.

The following abbreviations will be used.

The amino acids are represented by the symbols recommended by the Nomenclature Commission of the IUPAC-OUB, Biochemistry Section.

Ala : Alanine
Arg : Arginine
Asn : Asparagine
Asp : Aspartic acid
Gln : Glutamine
Glu : Glutaminic acid
Gly : Glycine
Ile : Isoleucine
Leu : Leucine
Lys : Lysine
Met : Methionine
Phe : Phenyl alanine
Ser : Serine
Thr : Threonine
Tyr : Tyrosine
Val : Valine With the exception of glycine, they all have the L-configuration.

CCM   thin layer chromatography

-continued

| OBzl | benzyl ester | 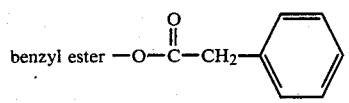 |
|---|---|---|
| Z | benzyl oxycarbonyl (carbamate) | 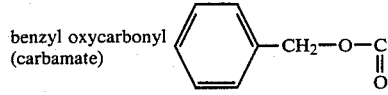 |
| Boc | tertiobutyloxy carbonyl (carbamate) | 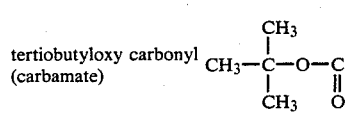 |
| DMF | dimethyl formamide | |
| NEM | N—ethyl morpholine | |
| TFA | trifluoroacetic acid | |
| MA | method of coupling with mixed anhydrides | |
| AcOEt | ethyl acetate | |
| OMe | OCH$_3$ | |
| Et$_2$O | ethyl ester | |
| ONSU | ester activated with N—hydroxy succinimide | 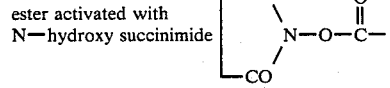 |

| | | |
|---|---|---|
| ONp | ester activated with ortho nitro phenol |  |
| Troc | trichloro ethoxy carbonyl (carbamate) | CCl$_3$—CH$_2$—O—C(=O) |
| Obu$^t$ | ester activated with tertiobutanol | —C(=O)—O—C(CH$_3$)$_3$ |
| MTS | 2,4,6-trimethyl-benzene-sulfonyl (mesityl-sulfonyl) | |
| OTcp | ester activated with 2,3,5 trichlorophenol | |
| OHBT | N—hydroxy benzotriazole | |
| ONb | ester activated with N—hydroxy 5-norbornene 2,3-dicarboximide | 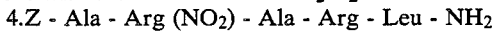 |
| NbOH | N—hydroxy 5-norbornene 2,3-dicarboximide | |
| BOP | hexacfluorophosphate of benzo triazolyl oxyphosphonium |  |
| DCHa | dicyclohexylamine | |
| DCU | dicyclohexylurea | |
| DCC or DCCI | dicyclohexylcarbodiimide | |
| TA | ambient temperature | |
| DIPEA | diisopropyl ethyl amine | |
| EPP | polypeptidic purity | |
| TFMSA | trifluoro methane sulfonic acid | |
| AAA | analysis of amino acids | |
| HPLC | high performance liquid chromatography | |
| Media of chromatography expressed in volumes: | | |
| BEW$_1$ | butanol, AcOH, H$_2$O, 71/7/21 | |
| BEW$_2$ | butanol, AcOH, H$_2$O 67/10/23 | |
| BPEW$_1$ | butanol, pyridine, AcOH, H$_2$O 50/12/12/25 | |
| EPAW | AcOEt, pyridine, HCO$_2$H, H$_2$O 63/21/10/6 | |
| BPEW$_2$ | butanol, pyridine, AcOH, H$_2$O 42/24/4/30 | |

Example I

Synthesis of H - Ala - Arg - Ala - Arg - Leu - NH$_2$ (fragment A)

1.

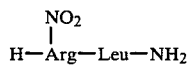

130 g of leucine amide (H-Leu-NH$_2$) are dissolved at ambient temperature in 1.5 l of DMF. 333 g of Boc-Arg(NO$_2$)—OH then 500 g of BOP are added. The pH is adjusted to 7 with pH paper (on small samples diluted with water) and with the aid of N-ethylmorpholine (NEM). The medium is stirred and the development of the reaction is followed by TLC. The reaction is terminated after 4 hours. The medium is evaporated to dryness in vacuo at 25° C. The residue is taken up in 1 liter of water and a solid is obtained which is washed with water, then with a 5% aqueous solution of NaHCO$_3$ with water, with ethyl acetate and, finally, the solid is dried in air. It is monitored by TLC.

The preceding solid is introduced into 2 l of a 50-50 by volume mixture of trifluoroacetic acid/methylene chloride. The medium is stirred for 10 mins. at ambient temperature and evaporated to dryness in vacuo at ambient temperature. The residue of evaporation is taken up in ether, drained, dried and monitored by TLC and NMR.

Yield : 339 g (90%) expressed in trifluoroacetate of a white solid.

2. H - Ala - Arg (NO$_2$) Leu - NH$_2$ 443 g of trifluoroacetate of H-Arg(NO$_2$)Leu - NH$_2$ are dissolved in 2 l of DMF. 200 g of Boc - Ala - OH, then 500 g of BOP are added. The pH is adjusted to 7 with pH paper (on small samples of the reaction medium) with the aid of NEM. The medium is stirred and the development of the reaction is followed by TLC. The reaction is terminated after 4 hrs. The medium is evaporated to dryness in vacuo at 25° C. The residue is taken up in 2 l of water and 2 l of ethyl acetate. The organic phase is washed with a 5% aqueous solution of NaHCO$_3$, with water, dried and evaporated. The tripeptide is recrystallized in ethyl acetate/ether, and finally dried in vacuo. It is monitored by TLC and NMR.

The preceding product, dried, is treated with a 50-50 (by volume) mixture of TFA-CH$_2$CL$_2$ under the conditions of the preceding Example I-1). Isolation is also effected under the same conditions.

Yield : 412 g (80%) expressed in trifluoroacetate of a white pulverulent product (monitored in TLC and NMR).

3. Arg (NO$_2$) - Ala - Arg (NO$_2$) - Leu - NH$_2$

From 515 g of H - Ala - Arg (NO$_2$) - Leu - NH$_2$ in 2.5 l of DMF and 333 g of Boc - Arg (NO$_2$) - OH and 500 g of BOP, 607 g (85%) of a white solid monitored by TLC and NMR are obtained by employing the operational conditions described in Example I-1, after treatment with the mixture TFA-CH$_2$Cl$_2$.

4. Z - Ala - Arg (NO$_2$) - Ala - Arg - Leu - NH$_2$

From 715 g of trifluoroacetate of H - Arg (NO$_2$) Ala - Arg (NO$_2$) - Leu - NH$_2$ in solution in 4 l of DMF and 233 g of Z - Ala - OH and 500 g of BOP employing the same technique as the one described in I-2 (and without treatment in that case by TFA - CH$_2$Cl$_2$), 612 g of Z - Ala - Arg (NO$_2$) - Ala - Arg (NO$_2$)Leu - NH$_2$ (76%) are obtained, after recrystallization in the DMF-ether mixture, in the form of a white pulverulent solid, monitored by TLC and NMR.

5. Ala - Arg - Ala - Arg - Leu - NH$_2$, 3 HCl 200 g of Z - Ala - Arg (NO$_2$) Ala - Arg (NO$_2$) - Leu - NH$_2$ (0.25 mole) are suspended in 2 l of methanol containing 0.8 mole of HCl. 40 g of Pd/C with 10% of Pd are added, and the medium is stirred in an atmosphere of hydrogen under a pressure of 1.2 bars, for 24 hours. After this interval of time, the end of the reaction is monitored by TLC. The catalyst is eliminated by filtration and the solvent is evaporated in vacuo at ambient temperature.

The solid residue is purified by chromatography over silica gel, using as elution medium the (50—12—12—25 by volume) mixture of butanol, pyridine, HO$_2$CCH$_3$,OH$_2$.

The fractions containing the pure product are collected together, evaporated and lyophilized.

Yield : 119 g (69%) of a white pulverulent solid

Monitored by : NMR, TLC
Analysis of aminoacids : Leu 1.03 (1); Arg 1.92 (2); Ala 1.95 (2).

EXAMPLE II synthesis of Boc-Gln-Glu (OBzl)-Arg-Gly-OH, HCl (fragment B'l)

1. Z-Arg (NO$_2$)-Gly-OBzl 3.37 g (0.01 mole) of tosylate of H-Gly-OBzl are dissolved in 15 ml of DMF, then 1 equivalent of NEM (1.3 ml) is added. This solution is added to a solution of 3.53 g (0.01 mole) of Z-Arg(NO$_2$)-OH in 15 ml of DMF containing 1 equivalent of NEM (1.3 ml).4.5 g (0.01 mole) of BOP are then added to the reaction mixture whose pH is then brought to 7 by addition of NEM and which is stirred at ambient temperature for 2 hours 30 minutes (the end of the reaction is determined by TLC : chloroform-methanol (3/1).

The reaction mixture is evaporated to dryness under reduced pressure (0.1 mm of Hg, i.e. 13.33 Pa) at a temperature lower than 30° C. The residue is taken up in 100 ml of ethyl acetate. This solution is poured into 120 ml of strongly stirred iced water. After a few instants of stirring, a precipitate is formed which is left overnight in the refrigerator.

The solid is drained and washed successively in the solid state with :
2×100 ml of an aqueous solution of sodium bicarbonate
2×100 ml of a 5% aqueous solution of SO$_4$HK-SO$_4$K$_2$
2×100 ml of water
2×100 ml of ether then dried in vacuo (13.33 Pa) up to a constant weight.
Yield: 4 g (80%)
Koffler melting point : 149° C.
TLC - chloroform-methanol (3/1) Rf: 0.73
Monitored by NMR 2. HCl-H-Arg-Gly-OH 100 g (0.2 mole) of Z-Arg (NO$_2$)-Gly-OBzl are suspended in a mixture of 600 ml of water, 600 ml of N hydrochloric acid and 100 ml of tetrahydrofuran.60 g of 10% Pd/C containing 50% humidity are added. This mixture is hydrogenated for 48 hours at ambient temperature and under a pressure of 2 kPa. The catalyst is then filtered and the aqueous solution is taken to pH 6.5 by addition of amberlite IR 45 resin (OH form). The resin is drained. The solution is then taken to pH 8.5 by addition of a fresh quantity of resin and the whole is stirred for 20 minutes in a rotavapor in vacuo (3.33 kPa). The resin is drained and the absence of ammonium chloride in the aqueous solution is checked by the Nesler test, then this solution is evaporated to dryness under reduced pressure (13.33 Pa) at a temperature lower than 30° C. A gummy residue is obtained which is dried overnight in a desiccator with phosphoric anhydride.

Yield : 43.19 g (80.6%)
TLC : ethyl acetate-pyridine-formic acid-water (40-21-10-6)
Rf : 0.1 Sakaguchi test positive (red spot)
Monitored by NMR.

3. Boc-Glu(OBzl)-Arg(HCl)-Gly-OH 41.5 g of HCl-H-Arg-Gly-OH (0.155 mole) are dissolved in a mixture of 400 ml of DMF and of 130 ml of water. The pH is adjusted to 7 by addition of N hydrochloric acid.

To this solution are simultaneously added :
a solution of 68.8 g of Boc-Glu(OBzl)-ONP (0.150 Ml) in a mixture of 100 ml of DMF and 40 ml of water.
a solution of 22.7 g of hydroxybenzotriazole (0.150 mole) in a mixture of 100 ml of DMF and 40 ml of water.
a solution of 37.8 ml of NEM (2×0.150 mole) in 100 ml of DMF.

The reaction mixture is stirred at ambient temperature and the reaction is followed in TLC (chloroform-methanol-acetic acid 95-5-9 and pyridine-ethyl acetate-formic acid-water 21-40-10-6).

After one hour of reaction, 13.76 g of Boc-Glu(OBzl)-ONP are added.

After 2 hours of reaction, 13.76 g of Boc-Glu-(OBzl)-ONP are added.

After 3 hours of reaction, 7 g of Boc-Glu(OBzl)-ONP are added and the reaction is continued for 1 hour.

The reaction mixture is then evaporated to dryness under reduced pressure (13.33 Pa) and at a temperature lower than 30° C. A thick oil is obtained which is dissolved in 500 ml of ethyl acetate. By addition of 1 liter of ether, a thick oil is formed. It is left to stand 24 hours in the refrigerator, then the liquid phase is decanted.

The residual oil is taken up in 500 ml of methanol. To this solution are added 500g of silica (70–230 mesh, i.e. 62–210 μm) and the solvent is evaporated by means of a rotavapor. The powder obtained is mixed with a 80-20 mixture of chloroform-methanol and the gel formed is introduced at the top of a column of silica gel (height 200 cm, diameter 85 mm) mounted in the 80-20 chloroformmethanol mixture.

The product is eluted with :
80-20 mixture of chloroform-methanol: 25 liters.
50-50 mixture of chloroform-methanol: 10 liters.
methanol : 30 liters.

The purification is followed by TLC (pyridine-ethylacetateformic acid-water, 21-40-10-6)

2 fractions are collected :
fraction A, 29.80 g
  TLC : pyridine-ethyl acetate-formic acid-water, 21-40-10-6; Rf : 0.75
  Monitored by NMR
  HPLC - EPP : 96.98%
  AAA : Glu 1.01-Gly 1.01-Arg 0.98
Fraction B, 36.82 g
  TLC : pyridine-ethyl acetate-formic acid-water, 21-40-10-6; Rf : 0.75
  1H NMR spectrum conformable
  HPLC - EPP : 99.61%
  AAA : Glu 0.93-Gly 0.99-Arg 1.08

4. Boc-Gln-Glu(OBzl)-Arg(HCl)-Gly-OH 52.78 g (0.09 mole) of the preceding product are suspended in 300 ml of methylene chloride. 300 ml of TFA are added at ambient temperature. The medium is kept for one hour at that temperature and finally the solvent and excess of TFA are evaporated in vacuo by means of a rotavapor without heat. The evaporation residue is taken up in ether (300 ml). It precipitates under the form of a white powdery product which is washed thoroughly in ether and dried in vacuo in a desiccator. The yield is quantitative and the product is used as is, for coupling with the glutamine. It is dissolved in 300 ml of DMF. 60 ml of water are added and the pH is returned to 7 by the NEM (monitorings conducted on small samples). 36.39 g of Boc-Gln-ONp (0.1 mole) are dissolved separately on 150 ml of DMF. On the other hand, 22.7 ml of NEM (0.2 mole) are also dissolved in 150 ml of DMF and 15.4 g of HOBT (0.1 mole) in 150 ml of DMF These last three solutions are added simultaneously for one hour to the first solution of the peptide in DMF/H$_2$O, making sure to keep the pH to between 6 and 7. The medium is stirred at ambient temperature for 4 hours and evaporated to dryness in vacuo at ambient temperature. The residue of evaporation is taken up 3 times in 150 ml ether. The resulting oil is dissolved in the upper phase of the 50% mixture of butanol and H$_2$O. The upper phase is washed twice with 200 ml of the lower phase. The lower phases are extracted with 50 ml of upper phase. The combined upper phases are evaporated to dryness in vacuo. The residue of evaporation is taken up in 150 ml of hot isopropanol and the product is precipitated by adding ether. 61.13 g (94.9%) of a product are obtained, which product is characterized by :

AAA : Gln(Glu) : 2.01 - Gly : 1.01 - Arg : 0.98HPLC: EPP =96.5%

1H monitoring by NMR - conformable
CCM (EPAW) Rf =0.58

EXAMPLE III

Boc-Glu(OBzl)-Ser-Asn-OH (fragment B'$_2$)

1. Boc-Ser-Asn-OBzl 17.65 g (0.0525 mole) of salt of TFA of H-Asn-OBzl are dissolved in 100 ml of DMF. The pH is brought to 7 by addition of NEM (about 5.5 ml). Then 19.2 g (0.0525 mole) o Boc-Ser-ONb are added. The pH is returned to 7 by addition of NEM. The mixture is stirred at ambient temperature with intermittent pH controls. After 4 hours, the reaction is completed (CCM). The reaction medium is evaporated to dryness in vacuo, the temperature being kept to below 30° C. The residue of evaporation is dissolved in 150 ml of ethyl acetate and the resulting solution is washed successively in 2×120 ml of a saturated aqueous solution of NaCl, 3×120 ml of a saturated aqueous solution of NaHCO$_3$, 3×120 ml of an aqueous solution of KHSO$_4$-K$_2$SO$_4$ and finally 1×120 ml of a saturated aqueous solution of NaCl. The organic phase dried over anhydrous MgSO$_4$ is evaporated to give a white powder which is dried in vacuo.

YIELD : 16.64 g (78%)
1H monitoring by NMR conformable
CCM : CHCl$_3$-methanol 3-1 - Rf : 0.6

2. Ser-Asn-OBzl, TFA 143.5 g (0.35 mole) of the product prepared according to the technique used in Example III No. 1, are dissolved in 700 ml of TFA. A light insoluble substance is filtered and the medium is kept for 30 mins at ambient temperature. The reaction medium is thereafter evaporated to dryness in vacuo at ambient temperature. The residue is taken up in 50 ml of ether and evaporated again. The residue precipitates into a white powder in the hexane-ether. The yield is quantitative - CCM : ClCl$_3$-methanol 3-1 - RF : 0.1.

3. Ser-Asn-OH,TFA 116 g (0.35 mole) of the preceding product are dissolved in 1.6 l of water. 35 g of 10% Pd/C containing 50% humidity are added. The medium is stirred for 24 hours at ambient temperature and under hydrogen atmosphere. After this period of time, another 20 g of the same catalyst is added and the reaction is continued for another 24 hours. The catalyst is eliminated by filtering and the water evaporated in vacuo at 30° C. The residue is taken up in 200 ml of methanol and evaporated to eliminate the rest of the water. After this last evaporation, the mixture is taken up in ether and a solid is obtained in these conditions. Said solid is drained and dried in vacuo.

Quantitative yield : CCM : EPAW - Rf : 0.13.

4. Boc-Glu-Ser-Asn-OH

O.35 mole of the preceding product (about 117 g) are dissolved in 300 ml of water. Then 0.7 mole of triethylamine is added. The pH is the 9 and the medium is diluted with 1.5 l of DMF. Then 0.35 mole (152 g) of Boc-Glu(OBzl)-ONSu in solution in 200 ml of DMF are introduced rapidly. The pH is kept to 7.2 by addition of triethylamine. The reaction is completed after 3 hours. The medium is evaporated to dryness in vacuo at 30° C. The residue is taken up in 3×1 liter of ether and finally dissolved in 1.5 l of the upper phase of the 50-50 butanol-water mixture. The solution is washed in 600 l of a 5% solution of KHSO$_4$—K$_2$SO$_4$, and three times in 300 ml of lower phase of the same butanol-water mixture and, finally with 300 ml of an NaCl saturated solution. The mixture is dried on anhydrous MgSO$_4$ and evaporated to dryness. The residue precipitates into a white powder in ether and hexane. After drying in vacuo, 120 g (63.8%) of a white powdery product are obtained.

1H monitoring by NMR : conformable
AAA : Asp : 1.02 - Ser : 0.90 - Glu : 1.09CCM (PBEW$_1$) - Rf : 0.55EPP : 96%

EXAMPLE IV

Synthesis of Boc-Ser-Arg-Gln-Gln-Gly-OH, HCl (fragment C)

1. Z-Gln-Gly-OMe

A suspension, cooled on an ice bath, of 75.36 g of HCl, H-Gly-OMe (0.6M) in one liter of DMF has 168.2 g of Z-Gln-OH (O.6M),256.41g of BOP (0.7M) and 165.4 ml of N-ethyl morpholine (1.3M) added thereto. After 20 hours of reaction at ambient temperature, the solution is concentrated under reduced pressure and the residue taken up with ethyl acetate. The organic solution is washed by :

a solution of sodium bicarbonate
a solution of sodium chloride
a solution of KHSO$_4$/K$_2$SO$_4$
a solution of sodium chloride The organic solution is dried over MgSO$_4$ and filtered. After 20 hours of rest, there is crystallization in each of the solutions. After filtration, the fractions coming from a crystallization in an aqueous medium are collected together and washed in water-saturated AcOEt to yield after filtration and drying in vacuo 7.78 g of product (m.p. 158°-159° C.).

The fraction coming from crystallation in AcOEt is washed in water-saturated AcOEt to yield, after filtration and drying in vacuo, 61.8 g of product (m.p.: 150°-154° C.).

The aqueous phase and the organic phase give an additional crystallization. These latter two products are collected together and washed as before to yield additional 38.05 g of comparable quality.

Overall yield : 107.63 g - monitored by NMR and TLC

2. HCl, H-Gln-Gly-OMe

A solution of 61.8 g of Z-Gln-Gly-OMe (175.9 mM) in 704 ml of DMF, 880 ml of methanol and to which ae added, with cooling by an ice bath, 176 ml of N HCl solution, then 3.1 g of 10% Pd/C. After 3 hr. 30 mins. of hydrogenation under excess pressure of 46.6 Pa, the catalyst is filtered over cellite and the solution is concentrated under reduced pressure. The residue is used directly in the following step.

3. Boc-Gln-Gln-Gly-OMe

A solution of the residue obtained in the preceding step (theoretically 175.9 mM) in 500 ml of DMF, cooled on an ice bath, has 77.6 g of Boc-Gln-ONp (211.1 mM), 26.4 g of hydroxy benzotriazole (211.1 mM) and N-ethylmorpholine added thereto until a pH of 7 is obtained. After 20 hrs. of reaction at ambient temperature, the solution sets to a mass. By addition of ethyl acetate, a precipitate is obtained which is drained, washed with AcOEt and dried in vacuo. 64.27 g of product are obtained, viz. a yield of 82%. Monitored by NMR and TLC.

4. TFA, H-Gln-Gln-Gly-OMe

A suspension cooled on an ice bath of 98.83 g of Boc-Gln-Gln-Gly-OMe (221.8 mM) in 300 ml of dichloromethane has 400 ml of TFA added thereto. After 30 mins. of reaction on an ice bath and one hour at ambient temperature, the solution is concentrated under reduced pressure up to half its initial volume and the residue is poured over stirred ether. After filtration, washing and drying in vacuo, 119 g of product are obtained.

5. Boc-Arg($NO_2$)-Gln-Gln-Gly-OMe

A solution of the 119 g of the preceding product in 1190 ml of DMF cooled on an ice bath has 77.91 g of Boc-Arg($NO_2$)-OH (244 mM), 97.51 g of BOP (266.2 mM) and N-ethylmorpholine added thereto until pH 7 is obtained. After 20 hrs. reaction at ambient temperature, the solution is poured over 8 liters of ethyl acetate. The precipitate obtained is filtered, washed with AcOEt then dried in vacuo. 153.7 g of product are obtained. Monitored by NMR and TLC.

6. TFA, H-Arg($NO_2$)-Gln-Gln-Gly-OMe

A suspension cooled on an ice bath of 153.7 g of Boc-Arg ($NO_2$)-Gln-Gln-Gly-OMe (theoretically 221.8 mM) in 600 ml of dichloromethane has 750 ml of TFA added thereto. After one hour at ambient temperature, 250 ml of TFA are further added and 30 mins. later, 250 ml of TFA are added. After a further hour of reaction, the solution is concentrated to one third of the initial volume and the residue is poured over 3 liters of ether with stirring. The precipitate formed is drained, washed with ether and dried in vacuo. 167 g of product are obtained.

7. Boc-Ser-Arg($NO_2$)-Gln-Gln-Gly-Ome

A solution on an ice bath of 167 g of TFA, H-Arg($NO_2$)-Gln-Gln-Gly-OMe (theoretically 221.8 mM) in 1.5 liters of DMF has added thereot 97.52 g of Boc-Ser-ONb (266.2 mM), 33.31 g of hydroxybenzotriazole (266.2 mM) and N ethylmorpholine until a pH of 7 is obtained. After 3 hrs. of reaction, at ambient temperature, part of the DMF is evaporated and the residual solution is poured over ethyl acetate with stirring. The precipitate is filtered, washed with ethyl acetate and dried in vacuo. 153.3 g of product are obtained, viz. a yield of 94.2% over 4 steps. Monitored by NMR and TLC.

8. Boc-Ser-Arg-Gln-Gln-OMe,AcOH

A solution of 153.3 g of Boc-Ser-Arq($NO_2$)-Gln-Gln-Gly-OMe (208.9 mM) in one liter of methanol, one liter of water and 500 ml of acetic acid is hydrogenated for 20 hours in the presence of 10 g of 10% Pd/C. After filtration of the catalyst and concentration of the solution, the residue taken up in water is lyophilized. 153 g of product are obtained, viz. a yield of 97.8%.

9. Boc-Ser-Arg-Gln-Gln-Gly-OH, HCl

A solution of 104.4 g of Boc-Ser-Arg-Gln-Gln-Gly-OMe (139.4 mM) in 2 liters of DMF has one liter of water, then 27.88 g of NaOH (697 mM) in 50 ml of water added thereto, with cooling by an ice bath. After 15 mins. of reaction at temperature close to 15° C., the product is neutralized by an N hydrochloric acid solution until a pH of 6.5 is obtained. After evaporation, the residue is triturated in ethyl acetate. The precipitate formed is drained, washed with AcOEt and dried in vacuo, then with air. 132.7 g of product are obtained.

Purification : 109 g of Boc-Ser-Arg-Gln-Gln-Gly-OH, HCl are purified by counter-current distribution in the n-butanol-methanol-water (4.01.5) mixture. After 700 transfers, the product is fractioned into three parts which, after evaporation and lyophilization, give: one fraction of 27.5 g and two fractions of 23.79 g and 16.90 g to be repurified.

Monitored by NMR and TLC - AAA : Ser: 0.91 - Arg : 0.97 - Gln(Glu) :2.05-Gly: 1.01.

EXAMPLE V

Boc-Leu-Gln-Asp-Ile-Met-NH-$NH_2$ (fragment D')

1. Boc-Met-NH-NH Troc 4.31 g (10 mM) of Boc-Met-OH, DCHa in solution in 50 ml of ethyl acetate are treated in the presence of 20 ml of water by a saturated solution of potassium bisulfate up to pH =3, the aqueous phase is extracted several time with ethyl acetate and the extracts dried over magnesium sulfate. To this solution are added 2.28 g (11 mM) of $H_2N$—NH-Troc(Troc=2,2,2-trichloro ethoxycarbonyl, this reagent being prepared in accordance with YAJIMA, Chem. Pharm. Bull. 1981, 19, 420).

After cooling in an ice bath, 2.37 g (11 mM) of 97% DCC in solution in 10 ml of ethyl acetate are added. After one night during which the product returns progressively to ambient temperature, the dicyclohexylurea is filtered and dried (2.04 g) and the organic solution is washed successively with the following aqueous solutions :

5% sulfate-bisulfate twice,ClNa 2M 2X 5% sodium bicarbonate twice, ClNa 3M twice and finally with water twice. After drying over magnesium sulfate and concentration of the solvent to virtual dryness, hexane is added until cloudiness begins and the product is kept at +4° C. overnight after which the precipitate formed in filtered, washed with a (4/1) mixture of hexane and ethyl acetate and dried in vacuo; 3.46 g (79%) are thus obtained : m.p.=92°-4° alpha D 25°=—32°—C=1, dioxane. TLC in chloroform-methanol-AcOH 95/5/3 - Rf =0.45

2. TFA, H-Met-NH-NH Troc 43.9 g (0.1 M) of Boc-Met-NH-NH-Troc in solution in 200 ml of dichloromethane and 20 ml of ethane dithiol are treated with an ice bath in a nitrogen atmosphere and with stirring by 200 ml of trifluoroacetic acid, the cold bath is removed and the product is left with stirring for one hour. The product is isolated by elimination of the volatile reagents firstly under 2.6 kPa then 13.33 Pa of pressure, the residual oil is taken up twice with 75 ml of isopropanol by evaporating in vacuo then washed twice by 75 ml of hexane by decantation after which it is dried in vacuo in the presence of potassium hydroxide overnight, after which it begins to solidify and is used as such in the following operation.

3. Boc-Ile-Met-NH-NH-Troc

The above oil (about 0.1M) of TFA, H-Met-NH-NH Troc in solution in 6500 ml of ethyl acetate and cooled in an ice bath is treated with 12.7 ml (0.1M) of N ethyl morpholine then 14.85 g (0.1M) of HOBt, 1H₂O then by 34.35 g (0.08M) of Boc-Ile-OSu followed by 12.7 ml (0.1M) of N ethylmorpholine (NEM). After ½ hour, the cold bath is removed and subsequently NEM is added periodically so as to maintain the apparent pH towards 7.

After 20 hrs., the reaction is complete and isolation is effected by successive washing with the following aqueous solutions: 5% sulfate-potassium bisulfate 3 times, water : three times, 5% sodium bicarbonate : 3 times and finally, water, up to neutrality.

After drying over magnesium sulfate and evaporation of the solvent in vacuo, 64 g of gum are obtained, chromatographed over a column of silica with dichloromethane containing from 0 to 1.5% of methanol. 30 g (68% of product having an HPLC purity of 98.9% and an NMR spectrum in accordance with the expected structure, are thus obtained. m.p. : 88°–92° C.

4. TFA, H-Ile-Met-NH-NH-Troc 27.6 g (50 nM) of Boc-Ile-Met-NH-NH-Troc in solution in 140 ml of dichloromethane and 14 ml of ethane dithiol are cooled with an ice bath and stirred in an atmosphere of nitrogen then 140 ml of trifluoroacetic acid are added thereto in 5-6 mins. The cold bath is removed and, after 45 mins., the product is isolated by evaporation of the reagents to a maximum, take-up of the residual oil by 2×60 ml of isopropanol followed by evaporation and finally by 2 washings with 60 ml of pentane. After drying for one night over potassium hydroxide in vacuo, an oil of vitreous appearance is obtained which is used in the following operation (30 g).

5. Boc-Asp(OBzl)-Ile-Met-NH-NH-Troc

The preceding 30 g of oil in solution in 250 ml of THF are treated with 6.4 ml (50 mM) of NEM and 18.9 (45 mM) of Boc-Asp(OBzl)$_{ON}$ SU. The apparent pH is adjusted between 6 and 7 by successive additions of NEM. After 4 hours, the product is isolated by evaporation of the THF, take-up in 400 ml of ethyl acetate followed by the same washings as the preceding homologue (3). The residue after drying and evaporation (36.5 g) is purified by chromatography over a column of silica with dichloromethane as solvent containing from 0 to 1.5% of methanol. 35 g (66%) of product presenting an NMR spectrum in accordance with the expected structure are thus obtained. m.p.=96°–100°.

6. Boc-Gln-Asp(OBzl)-Ile-Met-NH-NH-Troc 42 g (55 mM) of Boc-Asp(OBzl)-Ile-Met-NH-NH-Troc are dissolved in a mixture of 300 ml of anyhydrous methylene chloride and 30 ml of ethane-dithiol, and then treated in 15 to 20 mins. with 300 ml of TFA at ambient temperature under stirring. 45 mins. after the end of the mixing operation, the mixture is evaporated to dryness, taken up several times in anhydrous ether and decanted, then dried in vacuo in the presence of potassium hydroxide. The above-mentioned TFA salt is dissolved in 270 ml of DMF and cooled to +5°–+10° C. The pH is brought to 7 (paper pH) with N-ethylmorpholine. 8.4 g (55 mM) of hydrated HOBT, followed by 21 g of Boc-Gln-ONp (57 mM) are added and the pH is re-adjusted to 7. The temperature is brought back to 20° C. and the reaction is continued at that temperature for 4 hours, under stirring and at a pH of 7 maintained by N-ethylmorpholine. The solvent is evaporated in vacuo, the residue is taken up in H₂O, drained, washed with a sulphate-disulphate buffer, washed several times with water and dried in the open. The solid is ground and washed with ethyl acetate, drained, washed again with water and dried in vacuo in the presence of P₂O₅.

YIELD : 80% (39 g)

TLC : chloroform/acetone/AcOH 75/18/7

7. Boc-Leu-Gln-Asp(OBzl)-Ile-Met-NH-NH-Troc 39 g (44 mM) of the above Boc-Gln-Asp(OBzl)-Ile-Met-NH-NH-Troc are introduced in a well stirred mixture of 400 ml of iced TFA and 40 ml of ethane-dithiol, and then stirred for 45 mins. at ambient temperature. The solvent is evaporated, the residue is taken up in isopropanol and evaporated by completing the operation with a vane pump. Anyhydrous ether is added and the salt crystallizes; it is dried, washed in ether and dried in a desiccator in the presence of potassium hydroxide. The above salt of TFA is dissolved in 250 ml of DMF, the pH is adjusted to 7 (paper pH) by N-ethyl-morpholine, then 15 g (45.7 mM) of Boc-Leu-ONSU are added and the pH is kept to 7 by the N-ethyl-morpholine. After a period of three and a half hours, the DMF is evaporated in vacuo and the residue is taken up in water. The pH is brought to 2 by HCl 6 N. The solid is homogenized, drained, washed in water, dried, washed three times in ethyl acetate.

YIELD : 77% (34 g)

1H monitoring by NMR : conformable

TLC : chloroform-acetone-AcOH 75/18/7 single spot.

8. Boc-Leu-Gln-Asp(OBzl)-Ile-Met-NH-NH₂

17.9 g (17.5 mM) of Boc-Leu-Gln-Asp(OBzl)-Ile-Met-NH-NH-Troc are dissolved in a mixture of 200 ml of DMF and 50 ml of acetic acid and strongly stirred with mechanical stirring means. 11.5 g of powdered zinc (300 mesh=47 μm) are added in one operation and stirring is continued for 1 hour and 40 mins. at ambient temperature. The solid is drained, washed in DMF and the filtrate is introduced in 740 g of ice. The mixture is left to stand for one night, and then drained. The precipitate is washed with large quantities of water and dried in the open, then in a desiccator +P₂O₅.

YIELD : 78% (11.3 g)

1H monitoring by NMR - conformable

The resulting product is sufficiently pure (80-90%) to be used in the next step. If it is not, it is then purified by being dissolved in DMF and precipitated by an equal volume of n-butanol.

EXAMPLE VI

Boc-Arg(MTS)-Lys(Z)-Leu-NH-NH₂

1. Boc-Lys(Z)-Leu-OCH₃

To 1600 ml of ethyl acetate cooled down to +10° C. by an external iced bath and under stirring, are successively added : 53.88 g (0.297 mole) of H-Leu-OCH₃, HCl, 126 ml of N-ethyl-morpholine (1 mole), 44.5 g of OHBT (0.33 mole) and finally 166 g of Boc-Lys(Z)-OTcp (0.297 mole). The pH is kept to 6–7 by a further addition of N-ethyl-morpholine. The medium is stirred for one hour at +10° C. then for one night at ambient temperature. the reaction is then completed (CCM) and a slightly insoluble substance is eliminated by filtration. The solution is washed successively with 300 l of a 4% aqueous solution of K₂SO₄—KHSO₄, with 300 ml of a saturated solution of NaHCO₃, and finally with 300 ml of an aqueous solution of NaCl. The ether acetate solution is dried on anhydrous MgSO₄ and the solvent is evaporated in vacuo at 30° C. An oil is obtained which is purified by chromatography on 4 kg of Fine Merck silica (230-400 mesh, i.e. 37–62 μm) in a column of 7×210 cm. The product is first eluted with pure CHCl₃ until elimination of one head impurity. Then it is eluted with the CHCl₃ mixture containing 2% of CH₃OH. The fractions containing the pure product are re-grouped and the solvent is evaporated in vacuo. The oily residue is crystallized in the pentane-ether 50-50 mixture. The solid is drained and dried. The yield of pure product is 119 g (79%).

1H monitoring by NMR—conformable.

2. Lys(Z)-Leu-O-CH₃, TFA 10.15 g (20 nM) of Boc-Lys(Z)-Leu-O-CH₃ are suspended in 50 ml of methylene chloride. The mixture is cooled down to +5 -+10° C. and 50 ml of TFA are added. A homogeneous solution is then obtained which is kept for 50 mins. at ambient temperature under stirring. The medium is evaporated to dryness in vacuo without heating (30° C.) and the residual oil is washed in ether, which latter is in turn evaporated.

YIELD : 18.1 g of an oily product used as is in the next step.

3. Boc-Arg(MTS)-Lys(Z)-Leu-OCH₃

9.14 g (0.02 mole) of Boc-Arg(MTS)-OH are dissolved in 150 ml of THF. The solution is cooled in an ice bath and 2.82 g of OHNSu (N-hydroxy succinimide) and 5.02 g of DCCI are added. After 1 hour, the resulting precipitate of dicyclohexylurea is drained and then the solution is added to 150 ml of the THF of the product obtained in the preceding example (Example No. VI-2). The pH of the medium is kept to 7 by adding NEM. The medium is kept under stirring at ambient temperature for one night. The reaction is then completed (CCM) and the solvent is evaporated in vacuo at 30° C. The residue is taken up in 200 ml of ethyl acetate, and washed successively with 100 ml of a 5% aqueous solution of K₂SO₄—HKSO₄, 100 ml of an HNaCO₃ saturated aqueous solution, 100 ml of NaCl saturated aqueous solution and finally the organic phase is dried on anhydrous MgSO₄ and the solvent is evaporated in vacuo. The resulting oily residue is purified by chromatography on 600 g of Fine Merck silica (230-400 mesh, i.e. 37–62 μm) in a column of 4×95 cm. The impurities are first eluted with CHCl₃. The fractions containing the pure product are re-grouped and evaporated. The product cyrstallizes in pentane.

YIELD : 9 g (53%)

1H monitoring by NMR - conformable - TLC : (CHCl₃90, CH₃OH 10) -

Rf : 0.5

4. Boc-Arg(MTS)-Lys(Z)-Leu-NH-NH₂

7.1 g (0.0084 mole) of Boc-Arg(MTS)-lys(Z)-Leu-OCH₃ are dissolved in 110 ml of methanol. Then 20 ml of hydrazine hydrate are added under magnetic stirring at ambient temperature. The reaction is completed in 3 hours and the raction medium is poured into crushed ice under stirring. The mixture is left to stand overnight and the solid is drained and dried in a desiccator in vacuo in the presence of P₂O₅. 6.1 g (86%) of a white solid are thus obtained.

1H monitoring by NMR - conformable - TLC : CHCl₃—CH₃OH 90-10 - Rf : 0.25

EXAMPLE VII

Boc-Gln-Leu-Ser-Ala-OMe (fragment F₁)

1. Boc-Ser-Ala-OMe 25 g of H-Ala-OMe, HCl and 66 g. of Boc-Ser-ONb are dissolved in 500 ml DMF. The product is cooled in an ice bath and 25 ml of NEM, 24 g of N-hydroxy benzotriazole are added wtih magnetic stirring and the pH is maintained at 6.5 or 7 by addition of NEM. The product is stirred for 18 hrs. at ambient temperature. After TLC monitoring, the medium is evaporated to 90% (13.33 Pa 35° C.). The oil obtained is dissolved in 1.500 ml of chloroform, the product is washed with a solution of saturated sodium chloride (twice), 5% potassium sulfate/bisulfate solution (3 times), saturated sodium bicarbonate (5 times). The solution is dried over Na₂'SO₄ and evaporated to dryness. An oil is obtained which is dried to constant weight (30° C.13.33 Pa)

YIELD : 53.78 g- Monitored by TLC

2. H-Ser-Ala-OMe, TFA 52.8 g of Boc-Ser-Ala-OMe are dissolved in 100 ml of methylene chloride with magnetic stirring, being cooled with an ice bath. 250 ml of cooled TFA are added and the product is stirred for 20 mins. at ambient temperature and filtered. The filtrate is evaporated to dryness (35° water-jet pump). By addition of 2 l of ether, a white solid precipitates. It is drained, washed with ether (3 times), dried to constant weight (30°—13.33 Pa).

YIELD : 40.82 g

3. Boc-Leu-Ser-Ala-OMe 40 g of H-Ser-Ala-OMe, TFA and 32.9 g of Boc-Leu-OH, H₂O are dissolved in 400 ml of DMF. The product is cooled with an ice bath with magnetic stirring and 14.4 ml of NEM then 65.8 g of BOP and enough NEM to maintain the pH at 6.5–7 are added. The product is stirred for 2 hrs. at ambient temperature. After monitoring by TLC, the product is evaporated to dryness (13.33 Pa35° C.) and the oil obtained is dissolved in 1500 ml of chloroform, washed twice with a saturated NaCl solution, three times with 5% potassium sulfate / bisulfate, 3 times with saturated sodium bicarbonate, dried over Na₂SO₄, evaporated to dryness (30°—water-jet pump). The oil obtained is solidified in ether : Fraction A=29 g. A second jet B is obtained by addition of hexane, identical in TLC : B=13.7 g.

YIELD : 42.7 g. Monitored by NMR and TLC.

4. H-Leu-Ser-Ala-OMe, TFA 29 g of Boc-Leu-Ser-Ala-OMe are suspended in 50 ml of methylene chloride with magnetic stirring, being cooled by an ice bath. 100 ml of cooled TFA are added and, after dissolution, the product is stirred for 30 mins. at ambient temperature and filtered. The filtrate is evaporated to dryness (35° C. - water-jet pump). The oil obtained is solidified in ether (the solvent is changed several times). The product is dried to constant weight (30° C.-13.33 Pa)

YIELD : 30.2 g

5. Boc-Gln-Leu-Ser-Ala-OMe 30 g of H-Leu-Ser-Ala-OMe, TFA and 25.5 g of Boc-Gln-ONp are dissolved, with magnetic stirring, in 300 ml of DMF. The product is neutralized with 9.7 ml of NEM. 10 g of OHBt are added and the product is stirred for 2 hours at ambient temperature, maintaining the pH at 6.5-7 by addition of NEM.

After monitoring by TLC, the medium is concentrated to 90% (13.33 Pa—35°), taken up in 1000 ml of chloroform : a product precipitates into gel. The product is drained, washed, being taken up in 500 ml of chloroform (twice) then in ether (3 times). The product is dried to constant weight (13.33 Pa—30° C.).

YIELD : 32.1 g

TLC : chloroform/MeOH/AcOH : 9/2/0.5 - Rf =0.81

HPLC : EPP =91%

AAA : Ser : 0.86 - Glu : 1.02 - Ala : 0.99 - Leu : 0.99

EXAMPLE VIII

Boc-Tyr-Arg-Lyx(Z)-Val-Leu-Gly-OH, HCl
(fragment $G_1$)

1. Z-Leu-Gly-OCH$_3$ 0.22 mole of Z-Leu-OH are dissolved in 500 ml of DMF. To this solution are successively added:

25.11 g of HCl H-Gly-OCH$_3$ (0.2 mole)
28 ml of NEM
96 g of BOP (0.22 mole)

then the Ph is adjusted to 7 by addition of NEM.

The reaction mixture is stirred at ambient temperature, maintaining the pH at 7 by addition of NEM if necessary. The reaction is followed in TLC (chloroform-methanol-acetic acid 95-5-9). After 2 hours, the reaction is completed. The reaction mixture is evaporated to dryness under reduced pressure (26.66 Pa) and at a temperature lower than 30° C. The residue is taken up in ethyl acetate (1 liter).

The solution is washed successively with:

aqueous solution of bicarbonate (4×200 ml)
aqueous solution of SO$_4$HK-SO$_4$K$_2$(4×200 ml)
saturated aqueous solution of sodium chloride (2×200 ml)

dried over magnesium sulfate and evaporated to dryness under reduced pressure. The residue is taken up in ether (500 ml), triturated, drained, dried.

YIELD : 56.7 g (84.28%).

TLC: chloroform-methanol-acetic acid 95-5-3 Rf : 0.44

2. HCl-H-Leu-Gly-OCH$_3$ 56 g (0.166 mole) of Z-Leu-Gly-OCH$_3$ are dissolved in 900 ml of 0.23 N hydrochloric methanol. To this solution are added 6 g of 10% Pd/C containing 50% humidity. Hydrogenation is carried out for 24 hours at ambient temperature and under atmospheric pressure. The catalyst is filtered and the solution is evaporated to dryness under reduced pressure at a temperature lower than 30° C. The residue is taken up in ether (2×50 ml), is decanted and the product is dried in a desiccator in the presence of phosphoric anhydride. A white powder is obtained.

YIELD : 33.53 g (84.4%)

TLC : chloroform-methanol-acetic acid 90-20-9 Rf : 0.15

Monitored by NMR

3. Boc-Val-Leu-Gly-OCH$_3$ 28.24 g of Boc-Val-OH (0.13 mole) are dissolved in 400 ml of tetrahydrofuran cooled to −10° C. 14.45 ml (0.13 mole) of isobutyl chloroformate are then added. The mixture is stirred strongly at −10° C. for 15 mins. To this mixture is added a solution of tetrahydrofuran cooled to −10° C. containing 31.5 g of HCl H-Leu-Gly-OCH$_3$ (0.13 mole) previously neutralized by 14.45 ml of N methylmorpholine. Stirring is continued whilst cooling the reaction mixture in an ice bath (2 hours) then at ambient temperature for 2 hours. The reaction mixture is evaporated to dryness under reduced pressure at a temperature lower than 30° C. The residue is taken up in a 500 ml-500 ml mixture of ethyl acetate-water. The aqueous phase is decanted and the organic phase washed successively with an aqueous solution of sodium bicarbonate (2×50 ml)
an aqueous solution of SO$_4$KH-SO$_4$K$_2$(pH 2) (2 x 50 ml)
an aqueous solution of sodium chloride (50 ml)

then dried over magnesium sulfate and evaporated to dryness under reduced pressure at a temperature lower than 30° C. The residue is taken up with pentane (50 ml) drained and dried in vacuo (13.33Pa)

YIELD : 39.7 g (76%)

TLC : chloroform-acetone 75-25 Rf : 0.46

Monitored by NMR

4. TFA H-Val-Leu-Gly-OCH$_3$ 39 g of Boc-Val-Leu-Gly-OCH$_3$ (0.097 mole) are dissolved in 190 ml of TFA cooled in an ice bath. After dissolution, the ice bath is removed and the mixture is stirred for 30 mins. at ambient temperature. The product is evaporated to dryness under reduced pressure and the residue is taken up in ether (100 ml), triturated and the ether is decanted. This operation is repeated twice and the last traces of solvents are eliminated under reduced pressure (13.33 Pa).

YIELD : 44.8 g

TLC : chloroform-methanol-acetic acid 90-20-3 Rf : 0.36

5. Boc-Lys(Z)-Val-Leu-Gly-OCH$_3$ 25.55 g of TFA H-Val-Leu-Gly-OCH$_3$ (0.0615 mole) are dissolved in 200 ml of DMF. The solution is taken to pH 7 by addition of NEM. There are then added to this solution 32.47 g of Boc-Lys-(Z)-OTCP (0.058 mole) and 9 g of HOBT (0.059 mole). The pH of the reaction mixture is returned to 7 by addition of NEM. The product is stirred at ambient temperature, maintaining the pH at 7 by addition of NEM if necessary. The reaction is followed in TLC : chloroform-methanol, 90-10; chloroform-methanol-acetic acid, 90-20-3 (2 media).

After one hour, 1.96 g of Boc-Lys(Z)-OTCP (0.0035 mole) and 0.61 g of HOBT are added. The pH of the solution is returned to 7 by addition of NEM.

Two hours afterwards, the reaction is completed in TLC. The reaction mixture is then evaporated to dryness under reduced pressure (13.33 Pa) at a temperature lower then 30° C. The residue is taken up with 500 ml of water, triturated. The solid formed is drained then washed with 500 ml of aqueous solution of HKSO$_4$—K$_2$SO$_4$ (pH 2)
500 ml of a saturated aqeuous solution of sodium bicarbonate
200 ml of water then with ether (200 ml×2) and dried.

The impure product is chromatographed over a column of silica gel (5 cm×150 cm). It is eluted with the 80-20 mixture of chloroform-ethyl acetate (rate 600 ml/hr).

The good fractions determined in TLC are collected together, evaporated to dryness under reduced pressure. The residue is taken up in ether, triturated and the solid obtained drained. White powder, 35.14 g (86%).

TLC : chloroform-methanol 90-10 Rf : 0.62 chloroform-methanol-acetic acid, 87.7-9.4-2.8 Rf: 0.52

Monitored by NMR

AAA : Gly 1.00-Val 0.96-Leu 1.06-Lys 0.98

6. TFA H-Lys(Z)-Val-Leu-Gly-OCH$_3$ 15 g of Boc-Lys(Z)-Val-Leu-Gly-OCH$_3$ (22.6 mM) are dissolved in a mixture of TFA-methylene chloride (75 ml/75 ml). The product is stirred for 40 mins. at ambient temperature, then evaporated to dryness under reduced pressure at a temperature lower than 30° C.

The residue is taken up in ether containing 20% of hexane (100 ml). The solid formed is drained and dried. A white solid of 14.51 g is obtained.

YIELD : 94.7 %
TLC : chloroform/methanol/acetic acid (95/5/3) Rf: 0.12

7. Boc-Arg(HCl)-Lys(Z)-Val-Leu-Gly-OCH₃

14.1 of TFA H-Lys(Z)-Val-Ley-Gly-OCH₃ (21 mM) are dissolved in 50 ml of DMF. The solution is taken to pH 6-7 by addition of NEM. 6.57 g of Boc-Arg(HCl)-OH.1 H₂O (20 mM) and 10.6 g of BOP (24 mM) are then added to this solution. The pH of the reaction medium is returned to 6-7 by addition of NEM. The product is stirred at ambient temperature, maintaining the pH at 6-7 by addition of NEM if necessary. The reaction is followed in TLC : chloroform/methanol (80/20).

After 5 hrs., the reaction is completed. The reaction mixture is evaporated to dryness under reduced pressure (13.33 Pa) and at a temperature lower than 30° C. The oil obtained is taken up in 300 ml of ethyl acetate. The solid formed is drained and washed with ether (1st jet). Ether is added to the preceding filtrate; a solid precipitates which is drained (2nd jet): The two jets are identical in TLC. They are washed in the solid state by stirring for 1 hour with a mixture of 200 ml of ethyl acetate saturated water and 60 ml of water. The solid is drained, then washed with 60 ml of water and 300 ml of ether and dried.

YIELD: 78.7% (13.49 g)
TLC : chloroform/methanol (20/20)—Rf=0.32.
Monitored by NMR 8. TFA H-Arg(HCl)-Lys(Z)-Val-Leu-Gly-OCH₃

13.3 g of Boc-Arg(HCl)-Lys(Z)-Val-Leu-Gly-OCH₃ (15.5 mM) are dissolved in a (60 ml/60 ml) mixture of TFA-methylene chloride. The product is stirred for 40 mins. at ambient temperature then evaporated to dryness under reduced pressure at a temperature lower than 30° C. The residu is taken up by a (80/20 : 100 ml) mixture of ether-hexane. The solid formed is drained, washed with hexane and dried (weight: 15.13 g).

TLC : chloroform/methanol (3/1—Rf : 0.35

9. Boc-Tyr-Arg(HCl)-Lys(Z)-Val-Leu-Gly-OCH₃

15.5 mM of TFA H-Arg(HCl)-Lys(Z)-Val-Leu-Gly-OCH₃ are dissolved in 50 ml of DMF. The solution is taken to pH 6 by addition of NEM. 8.20 g of Boc-Tyr-OTCP (15.5×10 mM) and 2.41 g of HOBT (15.5×10 mM) are then added to this solution. The pH is returned to 6 by addition of NEM. The reaction mixture is stirred at ambient temperature, maintaining the pH at 6 by addition of NEM if necessary. The reaction is followed in TLC : chloroform/methanol (3/1). After 3 hrs., the reaction is terminated. The reaction mixture is evaporated to dryness under reduced pressure (13.33 Pa) and at a temperature lower than 30° C. The residual oil is taken up in ethyl acetate (300 ml). The gelatinous solid formed is drained, washed with ethyl acetate (100 ml), with ethyl acetate-ether (1/1 : 100 ml) then with ether (100 ml), finally with hexane (100 ml). The product is dried under reduced pressure up to constant weight. Yield : 96% (15.14 g).

TLC : chloroform/methanol (3/1)—RF : 0.47—Monitored by NMR

AAA : Gly : 0.95—Val : 0.98—Leu : 1.02—Lys : 1.01 Arg : 1.01—Tyr : 1.05
HPLC : 93.81 % EPP

10. Boc-Tyr-Arg(HCl)-Lys(Z)-Val-Leu-Gly-OH 7 g of Boc-Tyr-Arg(HCl)-Lys(Z)-Val-Leu-Gly-OCH₃ (6.86 mM) are dissolved in a mixture of 70 ml of dioxane and 35 ml of water. 6.4 ml of 4N sodium hydroxide (25.6 mM) : 3.7 equiv.) are added to this solution and the product is stirred for 30 mins. at ambient temperature. It is diluted with 200 ml of water and 800 ml of ethyl acetate. The mixture is then acidified to pH 3 by addition of (N) HCl. The ethyl aceeetate is decanted and the solid is drained (1st jet). The ethyl acetate is evaporated to dryness ; a 2nd jet is obtained. The two jets, identical in TLC, are collected together, washed with ether and dried.

YIELD : 74.7% (5.16 g)
TLC : chloroform/methanol (2/1) - Rf : 0.45
1H monitoring by NMR AAA : Bly : 1.00—Val : 0.97—Leu : 1.04—Tyr : 0.95—
Lys : 0.99—Arg : 1.05
HPLC - EPP 91.52:

EXAMPLE IX

Boc-Ile-Phe-Thr-Asn-Ser-NH-NH₂ (fragment H₁)

1. Boc-Asn-Ser-OMe

A solution of 23.32 g of Boc-Asn-OH (0.1M) and 19.7 g of NbOH (0.11M) in 250 ml of DMF, cooled on an ice bath, has 22.69 g of DCCI added thereto. After 3 hrs. reaction at ambient temperature, the DCU is filtered, cooled on an ice bath and 15.56 g of HCl, H-Ser-OMe are added. The pH is taken to, then maintained at 7 by addition of NEM. After 4 hrs. at ambient temperature and 20 hrs. at +4° C., the solution is concentrated under reduced pressure. The residue is taken up in the (50/50) mixture of AcOEt/n-butanol. The organic solution is washed successively with :

a saturated solution of sodium bicarbonate
a saturated solution of sodium chloride
a solution of 5% KHSO₄/K₂SO₄
a saturated solution of sodium chloride.

After drying over MgSO₄ and evaporation under reduced pressure, the residue is crystallized in the ether-hexane mixture. The product is filtered, washed with ether/hexane and dried in vacuo yielding 26.9 g of product.

YIELD : 80.8% - Monitored by NMR and TLC

2. TFA, H-Asn-Ser-OMe

A solution cooled on an ice bath of 13.5 g of Boc-Asn-Ser-OMe (40.5 mM) in 54 ml of dichloromethane has 81 ml of TFA added thereto. After one hour of reaction at ambient temperature, the solution is concentrated under reduced pressure, the residue is taken up with ether. A thick oil is obtained which is used in the following reaction.

3. Boc-Thr-Asn-Ser-OMe

A solution cooled on an ice bath of the crude product previously obtained in 300 ml of DMF has 14.09 g of Boc-Thr-ONSu (44.55 mM), 5.58 g of HOBt (41.3 mM) and NEM added thereto until a pH of 7 is obtained. After 20 hrs. of reaction at ambient temperature, the solution is concentrated under reduced pressure and the residue is taken up in the AcOEt/n butanol mixture. The organic solution is successively washed with :

a saturated solution of sodium bicarbonate
a saturated solution of sodium chloride
a solution of 5% KHSO₄/K₂SO₄
a saturated solution of sodium chloride.

After drying over MgSO₄, the solution is concentrated under reduced pressure and the residue crystallized in the ether/ hexane mixture. 8.28 g of product are obtained.

YIELD : 47%—Monitored by NMR and TLC

4. TFA, H-Thr-Asn-Ser-OMe

A solution cooled on an ice bath of 8 g of Boc-Thr-Asn-Ser-OMe in 32 ml of dichloromethane has 54 ml of TFA added thereto. After one hour of reaction at ambient temperature, the solution is concentrated under reduced pressure and the residue precipitated with ether. After filtration, it is used as such in the following reaction.

5. Boc-Phe-Thr-Asn-Ser-OMe

A solution of the precipitate obtained in the preceding step in 100 ml of DMF has 7.82 g of Boc-Phe-ONp (20.24 mM), 2.53 g of HOBt (18.71 mM) and N-ethyl morpholine added thereto, with cooling by an ice bath, until a pH of 7 is obtained. After 4 hrs., the solution is concentrated under reduced pressure and the residue is taken up in AcOEt. The organic solution is washed with :

a saturated solution of sodium bicarbonate
a saturated solution of sodium chloride
a solution of 5% $KHSO_4/K_2SO_4$
a saturated solution of sodium chloride After drying over $MgSO_4$, concentration of the organic phase, the residue is crystallized in ether. 10 g of product are obtained.

YIELD : 93.5% Monitored by TLC and NMR

6. TFA, H-Phe-Thr-Asn-Ser-OMe

A solution of 10 g of Boc-Phe-Thr-Asn-Ser-Ome (17.19 mM) in 40 ml of dichloromethane has 60 ml of TFA added thereto, with cooling by an ice bath. After one hour of reaction at ambient temperature, the product is precipitated with ether. The gum obtained after drying yields 5.15 g of product.

YIELD : 48.5%

7. Boc-Ile-Phe-Thr-Asn-Ser-OMe

A solution cooled on an ice bath of 5.14 g of TFA, H-Phe-Thr-Asn-Ser-OMe (8.78 mM) in 100 ml of DMF has 3.17 g of Boc-Ile-ONSU(9.66 mM), 1.30 g of HOBt 99.62 mM) and N-ethyl morpholine added thereto until a pH of 7 is obtained. After 20 hours of reaction at ambient temperature, the solution is concentrated under reduced pressure and the residue take up in ether gives a precipiate which is filtered and dried in vacuo. 5.24 g of product are obtained.

YIELD : 85.9% - Monitored by NMR and HPLC

8. Boc-Ile-Phe-Thr-Asn-Ser-NH-NH$_2$

A solution of 5 g of Boc-Ile-Phe-Thr-Asn-Ser-OMe (7.2 mM) in 40 ml of DMF and 200 of methanol cooled on an ice bath has 3.6 ml of an 80% solution of hydrazine hydrate added thereto. After 21 hours of reaction at ambient temperature, 0.9 ml of the same solution of hydrazine hydrate are added. After 3 more hours, the gel obtained is filtered, washed with methanol and dried in vacuo. 3.94 g of product are obtained.

YIELD : 78.8%—Monitored by NMR and TLC.

EXAMPLE X

Boc-Tyr-Ala-Asp(OBzl)-Ala-OH (fragment I)

1. Boc-Asp(OBzl)-Ala-OBut 362 g (0.02 mole) of hydrochoride of teriobutyl alaninate are suspended in 30 ml of acetonitrile. 2.52 ml of NEM are added then 8.4 g. (0.02 mole) of Boc-Asp(OBzl)ONSu. The pH is maintained at 6-6.5 by addition of NEM. Stirring is continued for 18 hours. After monitoring by TLC, the medium is evaporated to dryness, the oil is taken up in 50 ml of AcOEt, the solution washed twice with a solution of $KSHO_4/K_2SO_4$, then with salted water, dried over $Na_2SO_4$ and evaporated to dryness. The oil obtained is dissolved in hexane, a little solid is filtered and the filtrate is evaporated to dryness. The oil obtained is used as such.

TLC : $CHCl_3$/acetone/ACOH 80/15/5 Rf =0.8.

2. Boc-Ala-Asp(OBzl)-Ala-OH

The crude oil obtained previously is dissolved in 50 ml of iced TFA and stirred for 1 hr. 30 mins. at ambient temperature. the TFA is evaporated to a maximum and the residual oil is taken up three times in anhydrous ether and decanted. It is then dried in a desiccator in vacuo in the presence of pentane. A solid foam is formed which is crushed and returned to be dried.

9.4 g of crude product is obtained, used as such for coupling.

The above TFA salt is dissolved in a mixture of 20 ml of DMF and 18 ml of distilled water. NEM is added up to a pH of 7 (using the pH-meter). 4 g (0.014 mole) of Boc-Ala-ONSu in solution in 16 ml of DMF are introduced. The pH is maintained at 6.5-7 by addition of NEM. After 6 hrs.30 mins., the reaction is terminated (monitored by TLC). The solvent is evaporated to a maximum and the residue is taken up in a mixture of water and ethyl acetate. The organic phase is washed with a solution of $NaHCO_3$, with salted water, dried over $Na_2SO_4$ and evaporated to dryness. The residue is dissolved in ether and precipitated by hexane to give a gum which crystallizes after trituration.

The solid is drained and dried in air.

YIELD : 5.05 g TLC : $CHCl_3$-acetone-ACOH 80-15-5—Rf=0.28

3. Z-Tyr-Ala-Asp(OBzl)-Ala-OH 1 g (2 mmoles) of Boc-Ala-Asp(OBzl)-Ala-OH is introduced into 10 ml of stirred iced TFA.

After 30 mins. of stirring at ambient temperature, the TFA is evaporated to a maximum, the residue taken up twice in anhydrous ether and decanted, then dried in a desiccator in vacuo in the presence of potassium hydroxide. A solid foam is formed.

The crude product is dissolved in a mixture of 4 ml DMF and 2 ml of distilled water. NEM is added up to pH 7-7.5 1 g (2.4 mmoles) of Z-Tyr-ONSu is then added and the pH is maintained at 7.7-5 by NEM (pH-meter). After 2 hrs. 30 mins., after monitoring by TLC, the solvent is evaporated to a maximum at 40° C. The residue is taken up in ethyl acetate and washed with water; a little solid is eliminated and the ethyl acetate is washed with the mixture of sulfate bisulfate and salted water. After the product has been left for a few hours, a precipitate is formed which is drained, washed with ether and dried in air.

500 mg are thus obtained. A 2nd jet of 350 mg, slightly less pure, is obtained by concentration of the ethyl acetate.

TLC
chloroform-ACOH 3-1 Rf : 0.4
butanol-ACOH-$H_2O$ 72-7-2 Rf : 0.85
chloroform-acetone-ACOH 80-15-5 Rf : 0.1
HPLC 90.9% polypeptide purity
Monitored by NMR

EXAMPLE XI

Synthesis of H—Arg(MTS)—Lys(Z)—Leu—Leu—Gln—
—Asp(OBzl)—Ile—Met—Ser—Arg—Gln—Gln—Gly—
—Glu(OBzl)—Ser—Asn—Gln—Glu(OBzl)—Arg—Gly—

-continued
—Ala—Arg—Ala—Arg—Leu—NH$_2$ TFA, HCl (Peptide K$_1$)

1. Boc-Gln-Glu(OBzl)Arg-Gly-Ala-Arg-Ala-Arg-Leu-NH$_2$, HCl 6.53 g of H-Ala-Arg-Ala-Arg-Leu-NH$_2$, HCl (fragment A), namely $10^{-2}$ mole and 7.5 g of Boc-Gln-Glu(OBzl)-Arg-Gly-OH ($1.05 \times 10^{-2}$ mole) are dissolved in 100 ml of DMF. The pH is returned to 7 with addition of NEM and then 5.2 g of BOP ($10^{-2}$mole + 20%) are dded under stirring at ambient temperature. The pH is kept to 7 by intermittent additions of NEM. The reaction is completed after 4 hours. The medium is concentrated in vacuo at 35° C. and ethyl actate is added to the evaporation residue. A solid forms, which is then drained, and washed three times in ethyl acetate, three times in acetonitrile, then in ether, and dried in vacuo until a constant weight is reached. 116 g (87%) of a white product are obtained.

TLC : Butanol-Pyridine-AcOH-water (50/12/12/25)—Rf : 0.81 AcOEt-pyridine —H—CO$_2$H— water (40/20/10/6)—Rf : 0.89

AAA : Glu(Gln) : 2.02—Arg : 3.02—Leu : 0.95—Gly : 0.91—Ala : 2.1.

2. H-Gln-Glu(OBzl)-Arg-Gly-Ala-Arg-Ala-Arg-Leu-NH$_2$, TFA, HCl 11 g of the preceding peptide (Example XI No. 1) are suspended in 50 ml of cold methylene chloride. 60 ml of TFA cooled in an ice bath are added under magnetic stirring. The resulting solution is then stirred for 30 mins. at ambient temperature. Then 500 ml of ether are added and a white powdery solid precipitates instantly. Said solid is drained, washed four times with 200 ml of ether and dried until a constant weight is reached. In these conditions, a quantitative yield (11 g) of a white product is obtained.

TLC : Butanol-pyridone-AcOH-water (50/12/12/25)—Rf : 0.29

AcOEt-pyridine —H—CO$_2$H— water (63/21/10/6)—Rf : 0.11

3. Boc-Glu(OBzl)-Ser-Asn-Gln-Glu(OBzl)-Arg-Gly-Ala-Arg-Ala-Arg-Leu-NH$_2$, HCl 10.9 g ($8.1 \times 10^{-3}$ mole) of the preceding product (Example XI, 2) are dissolved under magnetic stirring in 120 ml of DMF. The pH is brought to 7 by addition of NEM. 6.49 g of Boc-Glu(OBzl)-Ser-Asn-OH and 4.35 g of BOP (excess : 20%) are added under stirring and at ambient temperature. The pH is kept to 7 by addition of NEM. The reaction is completed after 3 hours. The reaction product is concentrated in vacuo at 35° C. and the residue is precipitated with ethyl acetate. The resulting solid is drained and washed three times with ethyl acetate ($3 \times 100$ ml), three times in acetonitrile ($3 \times 100$ ml), in ether and then dried until a constant weight is reached. 12.6 g (90%) of a white solid are obtained. Monitoring by HPLC.

TLC : Butanol-pyridine-AcOH-water (60/12/12/25)—Rf : 0.49— AcOEt-pyridine —H—CO$_2$H— water(63/21/10/60)—RF : 0.40—

AAA : Glu(Gln) : 3.2—Ser : 0.92—Arg : 2.93—Leu : 0.98— Asp(Asn) : 0.98—Gly : 0.96—Ala : 2.00—

4. H-Glu(OBzl)-Ser-Asn-Gln-Glu(Ozl)-Arg-Gly-Ala-Arg-Ala-Arg-Leu-NH$_2$, TFA, HCl 50 ml of methylene chloride cooled beforehand by an ice bath, and 12.4 g of the preceding peptide (Example XI, 3) are suspended under magnetic stirring. 50 ml of TFA, cooled beforehand to 0° C. are then introduced. The product dissolves and stirring is continued for 30 mins. at ambient temperature. 500 ml of ether are then added. A white solid precipitates. It is drained, washed four times with 100 ml of ether and dried in vacuo until a constant weight is reached. 12.5 g (quantitative yield) of a white product are thus obtained.

TLC : Butanol-pyridine-AcOH-water (4/2/1/2)—Rf : 0.08—

5. Boc-Ser-Arg-Gln-Gln-Gly-Glu(OBzl)-Ser-Ans-Gln-Glu(OBzl)-Arg-Gly-Ala-Arg-Ala-Arg-Leu-NH$_2$, HCl 1.74 g ($10^{-3}$ mole) of the preceding product (Example XI, 4) are dissolved in 100 ml of DMF. The pH is brought to 7 by NEM. The medium is brought to 35° C. under magnetic stirring and 0.48 g of BOP and 0.783 g of Boc-Ser-Arg-Gln-Glu-Gly-OH ($10^{-3}$ mole 30 10%) are added in small portions for half-an-hour. 0.9 g of BOP are then added, the temperature being kept to 35° C. and the pH to 6.5 by addition of NEM. The progression of the reaction is monitored by HPLC. The reaction is completed in one hour and the medium is poured into 200 ml of ethyl acetate and left to stand overnight. A solid forms, which is drained, washed in ethyl acetate ($3 \times 50$ ml), then in ether and dried until a constant weight is reached. The yield is 2 g of a powdery white product.

TLC : Butanol-pyridine-AcOH-water (4/2/1/2)—Rf : 0.44

AAA : Ser : 1.91—Arg : 3.88—Glu(Gln) : 4.82—Gly : 2.01— Asp(Asn) : 0.91—Ala : 2.00—Leu : 0.98—

6. H-Ser-Arg-Gln-Gln-Gly-Glu(OBzl)-Ser-Asn-Gln-Glu(OBzl)-Arg-Gly-Ala-Arg-Ala-Arg-Leu-NH$_2$, TFA, HCl 25 g of the peptide described in Example XI, 5) are suspended in 100 ml of methylene chloride cooled down to 0° C. 50 ml of TFA at 0° C. are added, and after dissolution, the medium is kept for 30 mins. at ambient temperature. 500 ml of ether are then added. A white solid precipitates, which is drained, washed four times with 200 ml of ether and dried in vacuo until a constant weight is reached. 25 g(quantitative yield) of a white powdery product are thus obtained.

TLC : Butanol-pyridine-AcOH-water (4/2/1/2)—Rf : 0.05

7. Boc-Leu-Gln-Asp(OBzl)-Ile-Met-Ser-Arg-Gln-Gln-Gly-Glu(OBzl)-Ser-Asn- Gln-Glu(OBzl)-Arg-Gly-Ala-Arg-Ala-Arg-Leu-NH$_2$, HCl (a) Boc-Leu-Gln-Asp-(OBzl)-Ile-Met-NH-NH$_2$ 13.64 g of Boc-Leu-Gln-Asp(OBzl)-Ile-Met-NH-NH$_2$ (0.0166 mole) are dissolved in 100 ml of anhydrous DMSO and 200 ml of anhydrous DMF. The solution is cooled down to between −15° and −20° C. under stirring and inert atmosphere (nitrogen). 8 ml of an 8.25 N solution of HCl are added to the dioxanne and immediately after 2.5 ml of t.-butyl nitrite (i.e. 1.2 equivalent). The solution obtained is stirred under inert atmosphere (N$_2$) for 50 mins. at between −15° and −20° C. The pH of the medium is returned to 6.3–6.6 by addition of DIPEA. One quarter of the solution obtained is taken and kept in the freezer at −25° C. The rest is used in the next phase.

(b) Coupling of the axide 20.06 g of the peptide obtained in Example XI, 6 ($8.28 \times 10^{-3}$ mole) are dissolved in 70 ml of DMSO, then 100 ml of DMF are added. The medium is cooled to −10° C. and the pH is brought to 6.8 by addition of DIPEA. This cooled solution is then poured in 30 mins. in the remaining three quarters of the azide solution obtained in Example XI, 6(a), the temperature being kept to between −20° and −15° C. the pH is adjusted to 7 by addition of DIPEA. The medium is kept to −15° C. for 24 hours. Thereafter, the pH which had dropped to 6 is returned to 7 with DIPEA and the rest of the axide solution (the quarter which had been kept) is added in. The pH is returned to 7 by addition of DIPEA. After another 24 hours at that temperature (−20° to −15° C.) the medium is poured over 2 liters of cooled ethyl acetate under stirring. Stirring is continued for 30 mins. and the solid which has formed is drained and washed five times with 300 ml of ethyl acetate and three times in 300 ml of ether, and dried for one night in a desiccator in vacuo until a constant weight is reached. 22.08 g of a white powdery product is thus obtained (Yield : 87.16%).

TLC : BPEW1—Rf : 0.5

AAA : Leu : 1.98—Glu(Gln) : 5.92—Asp(Asn) : 1.98—Ile : 0.92 Met : 0.89Ser : 1.86Arg : 3.92Gly : 2.02Ala : 2.02-

8. H-Leu-Gln-Asp(OBzl)-Ile-Met-Ser-Arg-Glu-Gln-Gly-Glu(OBzl)-Ser-Asn-Gln-Glu(OBzl)-Arg-Gly-Ala-Arg-Ala-Arg-Leu-NH₂, TFA, HCl 10.25 g of the peptide obtained in Example XI, 7 are suspended in 80 ml of methylene chloride containing 4 ml of dithiol ethane. The suspension is stirred at ambient temperature under a stream of nitrogen. 80 ml of TFA are added. A very homogeneous solution is obtained which is kept for 40 mins. The medium is concentrated to one third of its initial volume in vacuo at 25° C. and poured into 40 ml of ether cooled down to 0° C. with stirring. A precipitate is obtained which is drained and washed three times with 100 ml of ether and dried in vacuo until a constant weight is reached. 9.89 g (96.1%) of a white powdery product is thus obtained.

TLC : BPEW1—Rf : 0.5

9. Boc-Arg(MTS)-Lys(Z)-Leu-Leu-Gln-Asp(OBzl)-Ile-Met-Ser-Arg-Gln-Gln-Gly-Glu(OBzl)-Ser-Asn-Gln-Glu(OBzl)-Arg-Gly-Ala-Arg-Ala-Arg-Leu, NH₂, HCl (a) Boc-Arg(MTS)-Lys(Z)-Leu-N₃

4.8 g of Boc-Arg(MTS)-Lys(Z)-Leu-NH—NH₂ (5.6×10⁻³ mole) are dissolved in 100 ml of DMF. The solution obtained is brought to between −15° and −20° C. under stirring. 2.9 ml of a solution 7.75N HCl in dioxanne, and immediately after 0.85 ml of t-butyl nitrite. The medium is stirred for 40 mins. at between −15° and −20° C. under a nitrogen atmosphere. The pH is neutralized to 6.5–6.9 by DIPEA. 15 ml of this solution (0.25 equivalent) is taken and kept at −20° C. under nitrogen. The remaining part is used in the following step.

(b) Coupling of the azide 9.83 g of the peptide obtained in Example XI, 8) are dissolved in 40 ml of anhydrous DMSO. 60 ml of DMF are then added. The solution is cooled down to −10° C. and the pH is brought to 6.6 by addition of DIPEA. This solution is thereafter poured in 15 mins. in the previous tripeptide azide solution, the temperature being kept at between −15° and −20° C. At the end of the addition, the pH is brought to 7 by DIPEA and the solution is kept for 24 hours at between −15° and −20° C. After this period of time, the rest of the azide solution (15 ml) is added and the pH is returned to 7 by DIPEA and the medium is kept for 24 hours at between −15 and −I20° C. This medium is then poured over 500 ml of cooled ethyl acetate and strongly stirred. A white solid substance forms slowly. It is drained and washed 3 times with 150 ml of ethyl acetate, and then with ether (2×150 ml), and dried in vacuo until a constant weight is reached. 9.65 g (80.4%) of a white powder are thus obtained. TLC : BPEW1—Rf : 0.54

AAA : Leu : 2.96—Glu(Gln) : 5.86 : Asp(Asn) : 1.96—Ile : 0.90— Met : 0.91—Ser : 1.86—Arg : 4.86—Gly : 2.06—Lys : 0.93 Ala : 2.00—

10. H-Arg(MTS)-Lys(Z)-Leu-Leu-Gln-Asp(OBzl)-Ile-Met-Ser-Arg-Gln-Gln-Gly-Glu(OBzl)-Ser-Asn-Gln-Glu(OBzl)-Arg-Gly-Ala-Arg-Ala-Arg-Leu-NH₂ TFA, HCl 8 g of the product obtained in Example XI, 9) are suspended in 50 ml of cold methylene chloride. 7 ml of dithiol ethane are added under stirring, and finally, 70 ml of TFA. The medium is kept for 40 mins. at ambient temperature, and then concentrated in vacuo to half its volume and poured over 500 ml of ether. The precipitate obtained is drained, washed 3 with 200 ml of ether and dried in vacuo until a constant is reached. It is used as is for the next coupling.

EXAMPLE XII

Synthesis of
Boc-Ile-Phe-Asn-Thr-Ser-Tyr-Arg-Lys(Z)-Val-Leu-Gly-Gln-Leu-Ser-Ala-OH, HCl (peptide J)

1. H-Gln-Leu-Ser-Ala-OCH₃, TFA 10.3 g (18.8 mM) of Boc-Gln-Leu-Ser-Ala-OCH₃ are stirred for 35 mins. in 100 of dichloromethane containing 100 ml of TFA. The reaction medium is concentrated in vacuo to about 50 ml and poured over 300 lm of ether. The precipitate obtained is drained and washed with 3 times 100 ml of ether. It is then dried in vacuo until a constant weight is reached. The yield is quantitative (10.4g) and the product is used as is in the next coupling.

2. Boc-Tyr-Arg(Z)-Val-Leu-Gly-Gln-Leu-Ser-Ala-OCH₃, HCl

To the TFA salt obtained hereinabove, dissolved in 200 ml of dimentylformamide and neutralized with N-ethylmorpholine are added 18.9 g (18.8 mM) of Boc-Tyr-Arg-Lys(Z)-Val-Leu-Gly-OH then 9.2 g of BOP(21 mM) then NEM to take the pH of the reaction medium to around 6. After 4 hrs. stirring, the reaction medium is poured over 1 liter of AcOEt. The precipitate obtained in filtered, washed three times with 100 ml of AcOEt, then 3 times with 100 ml of Et20 then it is dried in vacuo.

24.16 g of product are obtained. Yield: 90% TLC Rf : 0.20 (BEW1)—Alpha D : −17.6°—(Cc : 1—DMF with 5% AcOH)-product identified by 1H NMR and AAA : Ser: 1.01—Glu : 0.99— Gly : 1.06—Ala : 1.01—Val: 0.98—Leu K: 1.97—Tyr : 1.00— Lys : 0.98—Arg : 0.99—HPLC in reverse phase (EPP : 92%)

3. H-Tyr-Arg-Lys(Z)-Val-Leu-Gly-Gln-Leu-Ser-Arg-OCH₃, HCl, TFA 8.66 g (6.1 mM) of the above product are stirred for 35 mins. in 37 ml of dichloromethane plus 3.5 ml of anisole plus 40 ml of TFA. After concentration in vacuo by half, the residue is poured over 300 ml of iced ether; the white precipitate obtained is filtered, washed with ether and dried in vacuo over potassium hydroxide.

Weight : 8.68 g—Yield : 100%

4. Boc-Ile-Phe-Thr-Asn-Ser-N₃

5.94 (8.55 mM) of Boc-Ile-Phe-Thr-Asn-Ser-NH-NH₂ are dissolved in 27 ml of DMSO plus 37 ml of DMF. After cooling to −25° C., 6.1 ml of a 5.6N HCl/dioxane solution, then 1.23 ml of tertiobutyl nitrite (1.2 equiv.) prediluted in 5 ml of DMF precooled to −20° C., are added. After 1 hr. 15 mins of stirring between −20° C. and −25° C., 6.1 ml of diisopropylethylamine (DIPEA) are added to take the pH to around 6, then 3 ml of DMF are added to take the volume to 85 ml and this solution is conserved at −25° C.

5. Boc-Ile-Phe-Thr-Asn-Ser-Tyr-Arg-Lys(Z)-Val-Leu-Gly-Gln-Leu-Ser-Ala-OCH₃, HCl

The TFA salt obtained in Example XI-3 is dissolved in 70 ml of DMF and neutralized by DIPEA then added in 15 mins. to 70 ml of the azide solution obtained hereinabove at −20° C. Then DIPEA is added to take the pH towards 7, the product is stirred for one hour at −20C, then the medium is conserved at −12° C. After 22 hrs., 5 ml of the azide solution are added and the pH is raised towards 7 by DIPEA. After 45 hrs., the remaining azide solution is added and the pH is raised towards 7 by DIPEA. After 74 hrs., the reaction medium is poured over 1200 ml of ethyl acetate. The white precipitate obtained is filtered, washed with ethyl acetate then with ether, then dried in vacuo. Weight: 10.46 g—Yield: 86%

By concentration of the mother liquors and reprecipitation by an ethyl acetate/ether mixture, a second jet is obtained which makes it possible to have an overall yield of 95%. The coupling product is identified by 1H NMR and AAA : Asp : 1.02—Thr : 1.03— Ser : 1.91— Glu : 0.97—Gly : 1.06—Ala : 1.06—Val : 1.00 —Ile : 0.94—Leu : 1.98—Tye : 1.04—Phe : 1.02—Lys : 0.94— Arg : 1.02—TLC Rf : 0.20 (BEW1)—HPLC in reverse phase (EPP : 90%)

6. Boc-Ile-Phe-Thr-Asn-Ser-Tyr-Arg-Lys(Z)-Val-Leu-Gly-Gln-Leu-Ser-Ala-OH, HCl 5.3 g (2.7 mM) of the product obtained hereinabove are dissolved in 40 ml of DMSO plus 6 ml of water; 10 ml of 1N of sodium hydroxide are added drop by drop, the product is stirred for 30 mins. Then neutralized with 10 ml of 1N hydrchloric acid. The reaction medium is poured over one liter of ethyl acetate. The precipitate obtained is filtered, washed 4 times with ethyl acetate then twice with water, then 4 times with ether, then it is dried in vacuo over P₂O₅.

Weight : 4.56 g—Yield : 86 %—Product identified by IH NMR and AAA—TLC : Rf : 0.5 BEW1

EXAMPLE XIII

Synthesis of Z—Tyr—Ala—Asp(OBzl)—Ala—Ile—Phe—
—Thr—Asn—Ser—Tyr—Arg—Lys(Z)—Val—Leu—Gly—
—Gln—Leu—Ser—Ala—Arg(MTS)—Lys(Z)—Leu—Leu—
—Gln—Asp(OBzl)—Ile—Met—Ser—Arg—Gln—Gln—
—Gly—Glu(OBzl)—Ser—Asn—Gln—Glu(OBzl)—Arg—
—Gly—Ala—Arg—Ala—Arg—Leu—NH₂,
HCl (GRF 1-44 protected)

1. Boc-Ile-Phe-Thr-Asn-Ser-Tyr-Arg-Lys(Z)-Val-Leu-Gly-Gln-Leu-Ser-Ala-Arg(MTS)-Lys(Z)-Leu-Leu-Gln-Asp(OBZL)-Ile-Met-Ser-Arg-Gln-Gln-Gly-Glu(OBzl)-Ser-Asn-Gln-Glu(OBzl)-Arg-Gly-Ala-Arg-Ala-Arg-Leu-NH₂, HCl 6.6 g of the TFA salt of the penta ecosa peptide obtained in Example XI, 10° (1.9×10⁻³mole) are dissolved in 36 ml of DMSO. 90 ml of DMF are then added and the pH of the medium is returned to 7 by addition of NEM. After what, 1.0 g of BOP are added, followed by 3.8 g (1.9×10⁻³ mole) of the peptide of Example XII 6). The pH of the medium is returned to 6 by addition of NEM. After stirring for 20 hours at ambient temperature under inert atmosphere (N₂), another 0.5 g of BOP is added. 12 hours later, the reaction is completed and the reaction medium is poured over 600 ml of ethyl acetate. The precipitate obtained is filtered and washed with ethyl acetate (3 times 100 ml) and dried in vacuo until a constant weight is reached.

The yield is 95 g (90%).

The product is identified by HPLC and AAA.

2. H-Ile-Phe-Thr-Asn-Ser-Tyr-Arg-Lys(Z)-Val-Leu-Gly-Gln-Leu-Ser-Ala-Arg(MTS)-Lys(Z)-Leu-Leu-Gln-Asp(OBzl)-Ile-Met-Ser-Arg-Gln-Gly-Glu(OBzl)-Ser-Asn-Gln-Glu(OBzl)-Arg-Gly-Ala-Arg-Ala-Arg-Leu-NH₂, HCl, TFA.

9.1 g of the product obtained above are stirred for 30 mins. in 100 ml of TFA with 5 ml of dithiol ethane. Then the reaction medium is poured over 500 ml of iced ether. The precipitate obtained is filtered, washed with Et₂O, and then dried over potassium hydroxide.

Yield : 100%.

3. Protected GRF-1-44

To 9.10 g of the preceding TFA salt (1.66 mM) in solution in 50 ml of DMF and 50 ml of DMSO and neutralized by NEM, are added 1.18 g of the peptide described in Example X-3 (1.78 mM) and 0.79 g of BOP (1.78 mM); the pH is maintained at around 6 by NEM. After 23 hrs. at ambient temperature, the reaction medium is poured over 600 ml of AcOEt. The precipitate formed in filtered, washed with ethyl acetate, then with ether and finally dried in vacuo.

Yield : 8.54 g (84%)

Monitored by NMR and TLC : - AAA : Asp : 4.2—Thr : 0.92—Ser : 4.02 —Glu : 7.37 (for 7)— Gly : 3.14 (for 3)—Ala : 5.11—Val : 1.01— Met : 0.61—Ile : 1.84—Leu : 4.98—Tyr : 1.87—Phe : 0.95— Arg : 5.90

EXAMPLE XIV

Deprotection of GRF 1-44 :

4.5 g of the product obtained in accordance with Example XIII 4 are stirred for one hour at 0° in 180 ml of TFA containing 19.8 ml of TFMSA, 27 ml of thioanisole and 11 ml of metacresol. 1 1. of ether is then added. The precipitate obtained is filtered, washed with ether then dried one hour in vacuo in the presence of potassium hydroxide. The product is redissolved in 200 ml of water and ion exchanger resin Amberlite IR 45 (in the form of acetate) is added in order to return the pH to 4.5. The medium is stirred for 30 mins. at ambient temperature. The resin is filtered, washed with water and the filtrates concentrated to 50 ml when lyophilized. Yield : 3.85 g. Monitored by NMR of the disappearance of the protector groups Z and OBzl.

TLC (BEPW1) : majority spot Rf 0.38

Polypeptide purity monitored by HPLC : 65%.

EXAMPLE XV

Purification of the GRF 1-44

The deprotected peptide obtained in the preceding Example (XIV) is subjected to a chromatography over Sephadex G 50 gel (fine), using 30% acetic acid as eluent.

The fractions containing the expected peptide are collected together, evaporated and lyophilized.

The lyophilizate thus obtained is purified in turn by a chromatography over a cation exchanger of the CM-32 carboxymethylcellulose (Whatman) type, using a linear grdient of ammonium acetate of between 0.1M (pH 4.5) and 0.4M (pH 6.5). For example, for one charge of 1 g of peptides to be purified, a chromatography column having a bed volume of about 50 ml for a height fo 20 cm will be used.

The fractions containing the peptide with a degree of purity ≧80% (HPLC) are collected together and lyophilized up to constant weight (in order to eliminate the CH$_3$CO$_2$NH$_4$ buffer).

Finally, the preceding lyophilizate is subjected to a partition chromatography, using as support of the stationary liquid phase, fine Sephadex G 50 and with the aid of the following system of solvents : n-butanol/ethanol/pyridine/0.2N acetic acid in the proportion of 4/1/1/7 (in volume). The fractions of chromaography are monitored by HPLC and those of which the titer of purity is ≧95% are collected toghether and lyophilized. The yield in isolated product is 35%.

The product is finally monitored by analysis of the amino acids :

Tyr : 1.91 (2)
Ala : 4.88 (5)
Aln, Asp : 3.86 (4)
Ile : 1.96 (2)
Phe : 0.93 (1)
Thr : 1.02 (1)
Ser : 3.88 (4)
Arg : 5.89 (6)
Lys : 1.98 (2)
Val : 1.01 (1)
Leu : 5.10 (5)
Gly : 2.98 (3)
Gln , Glu : 6.82 (7)
Met : 0.91 (1)

What we claim is:

1. A process for the synthesis, in liquid phase and by fragments , of hGRF 1-44 and hGRF 1-40, wherein said process consists in coupling, one after the other and in the order of the sequence of the GRF, (1) on the one hand, the following fragments :

| | | |
|---|---|---|
| H—Ala—Arg—Ala—Arg—Leu—NH$_2$ | called Fragment A | hGRF (40-44) or alaninamide |
| H—Gln—Glu—Arg—Gly—OH | called Fragment B'$_1$ | hGRF (36-39) |
| H—Glu—Ser—Asn—OH | called Fragment B'$_2$ | hGRF (33-35) |
| H—Ser—Arg—Gln—Gln—Gly—OH | called Fragment C | hGRF (28-32) |
| H—Leu—Gln—Asp—Ile—Met—OH | called Fragment D' | hGRF (23-27) |
| H—Arg—Lys—Leu—OH | called Fragment E'$_1$ | hGRF (20-22) | to obtain the peptide K[hpGRF (20-44] or the corresponding peptide having the sequence (20-40) and (2) on the other hand, the following fragments :

| | | |
|---|---|---|
| H—Gln—Leu—Ser—Ala | called Fragment F$_1$ | hGRF (16-19) |
| H—Tyr—Arg—Lys—Val—Leu—Gly OH | called Fragment G$_1$ | hGRF (10-15) |
| H—Ile—Phe—Thr—Asn—Ser—OH | called Fragment H$_1$ | hGRF (5-9) | to obtain the peptide J [hGRF (5-19)] and thereafter to couple together the peptides J and K$_1$ in order to form the peptide having the sequence hGRF (5-44) or hGRF (5-40) and finally to couple the resulting peptide with the peptide H-Tyr-Ala-Asp-Ala-OH, called fragment I hGRF (1-4) and process wherein, in addition, in said fragments :

(a) the side acid functions of the aspartic and glutamic acids and the side amine function of the lysine are protected by protector groups stable in the conditions of deprotection of the group Boc, tertiobutyloxycarbonyl);

(b) the guanidine function of the arginine in position 20 is protected by the MTS group (2,4,6-trimethyl phenylsulfonyl) and the guanidine function of the other arginines is protected by protonation; and (c) the N-terminal amino acid is protected on the amine by the Boc group, selectively eliminating the group Boc from the N-terminal amine of the peptide in phase of elongation by hydrolysis with trifluoroacetic acid, said coupling being effected in an aprotic polar solvent and eliminating, at the end of sequence, all the protector groups by hydrolysis with the aid of a 0.1 to 1M solution of methanesulfonic or trifluoromethanesulfonic acid in trifluoroacetic acid.

2. The process of claim 1, wherein, after each coupling, the product obtained is isolated from the reaction medium by precipitation with the aid of an insolubilizing solvent.

3. The process of claim 1, wherein the crude product of reaction is purified by counter-current distribution and permeation chromatography over gel.

4. The process of claim 1, wherein the coupling is with the help of hexafluorophosphate of benzotriazolyloxyphosphonium (BOP) or dichyclohexyl-carbodiimide in the presence of 1-hydroxy-benzotriazole (coupling agent) or by activation with carboxyazides, in an appropriate solvent such as diemthylformamide or dimethylsulfoxyde.

* * * * *